US011406595B2

(12) United States Patent
Subramanian et al.

(10) Patent No.: US 11,406,595 B2
(45) Date of Patent: Aug. 9, 2022

(54) HIGHLY STABLE COLLOID FROM AQUEOUS SOLUTIONS OF SMALL ORGANIC MOLECULES

(71) Applicant: University of Maryland, College Park, College Park, MD (US)

(72) Inventors: Deepa Subramanian, Greenbelt, MD (US); Mikhail A. Anisimov, Beltsville, MD (US)

(73) Assignee: University of Maryland, College Park, College Park, MD (US)

( * ) Notice: Subject to any disclaimer, the term of this patent is extended or adjusted under 35 U.S.C. 154(b) by 377 days.

(21) Appl. No.: 13/899,126

(22) Filed: May 21, 2013

(65) Prior Publication Data

US 2014/0004194 A1 Jan. 2, 2014

Related U.S. Application Data

(60) Provisional application No. 61/649,755, filed on May 21, 2012.

(51) Int. Cl.
*A61K 9/08* (2006.01)
*B01J 13/00* (2006.01)
*A61K 47/69* (2017.01)

(52) U.S. Cl.
CPC ............. *A61K 9/08* (2013.01); *B01J 13/0034* (2013.01); *A61K 47/6905* (2017.08)

(58) Field of Classification Search
CPC .................. A61K 9/08; A61K 47/6905; A61K 47/48792; B01J 13/0034
USPC ......................................................... 424/489
See application file for complete search history.

(56) References Cited

U.S. PATENT DOCUMENTS

| 4,863,633 | A | * | 9/1989 | Colborn et al. .......... 252/186.35 |
| 5,718,905 | A | * | 2/1998 | Skiba ..................... A61K 8/738 |
| | | | | 264/4.1 |
| 2001/0034333 | A1* | | 10/2001 | Kosak .................. A61K 9/1075 |
| | | | | 514/44 A |
| 2004/0092102 | A1* | | 5/2004 | Li et al. ........................ 438/689 |
| 2009/0004262 | A1* | | 1/2009 | Shaw .................... A61K 9/1623 |
| | | | | 424/456 |
| 2013/0213435 | A1* | | 8/2013 | Hanson et al. .................... 134/6 |

FOREIGN PATENT DOCUMENTS

CA          2309326 C  * 12/2010  ........... A61K 9/0019

OTHER PUBLICATIONS

Feller et al., "Constant pressure molecular dynamics simulation: The Langevin piston method," The Journal of Chemical Physics, 1995, vol. 103, No. 11, pp. 4613-4621.
Martyna et al., "Constant pressure molecular dynamics algorithms," The Journal of Chemical Physics, 1994, vol. 101, No. 5, pp. 4177-4189.
Humphrey et al., "VMD: Visual molecular dynamics," Journal of Molecular Graphics, 1996, vol. 14, pp. 33-38.
Kasraian et al., "Thermal analysis of the tertiary butyl alcohol-water system and its implications on freeze-drying," Pharmaceutical Research, 1995, vol. 12, No. 4, pp. 484-490.
Kipkemboi et al., "Densities and viscosities of binary aqueous mixtures of nonelectrolytes: tert-butyl alcohol and tert-butylamine," Canadian Journal of Chemistry, 1994, vol. 72, pp. 1937-1945.
Nakanishi et al., "Partial molal volumes of butyl alcohols and of related compounds in aqueous solution," Bulletin of the Chemical Society of Japan, 1960, vol. 33, No. 6, pp. 793-797.
Roux et al., "Microheterogeneity in aqueous-organic solutions: Heat capacities, volumes and expansibilities of some alcohols, aminoalcohol and tertiary amines in water," Journal of Solution Chemistry, 1980, vol. 9, No. 9, pp. 629-647.
Anisimov et al., "An Anomaly in the heat capacity and structural phase transformation of the ordering type in an aqueous solution of t-butanol," Journal of Structural Chemistry, 1977, vol. 18, No. 5, pp. 663-670.
De Visser et al., "The heat capacities, volumes and expansibilities of tert-butyl alcohol-water mixtures from 6 to 65° C," Canadian Journal of Chemistry, 1977, vol. 55, No. 5, pp. 856-862.
Koga et al., "Excess partial molar enthalpies of water in water-tert-butanol mixtures," Canadian Journal of Chemistry, 1988, vol. 66, No. 12, pp. 3171-3175.
Koga et al., "Differential heats of dilution of tert-butanol in water-tert-butanol mixtures at 26.90° C," Canadian Journal of Chemistry, 1986, vol. 64, No. 1, pp. 206-207.
Koga et al., "Excess partial molar enthalpies of tert-butanol in water-tert-butanol mixtures," Canadian Journal of Chemistry, 1988, vol. 66, No. 5, pp. 1187-1193.
Koga et al., "Excess partial molar free energies and entropies in aqueous tert-Butyl alcohol solutions at 25° C," Journal of Physical Chemistry, 1990, vol. 94, pp. 7700-7706.
Tamura et al., "Compressibilities of aqueous tert-butanol in water-rich region at 25° C: Partial molar fluctuations and mixing schemes," Physical Chemistry Chemical Physics, 1999, vol. 1, pp. 121-126.
Stillinger, "Structure in aqueous solutions of nonpolar solutes from the standpoint of scales-particle theory," Journal of Solution Chemistry, 1973, vol. 2, Nos. 2-3, pp. 141-158.
Lum et al., "Hydrophobicity at small and large length scales," Journal of Physical Chemistry B, 1999, vol. 103, pp. 4570-4577.
Habich et al., "Do stable nanobubbles exist in mixtures of organic solvent and water?," Journal of Physical Chemistry B, 2010, vol. 114, pp. 6962-6967.
Jin et al., "Slow relaxation mode in mixtures of water and organic molecules: Supramolecular structures or nanobubbles?," Journal of Physical Chemistry B, 2007, vol. 111, pp. 2255-2261.

(Continued)

*Primary Examiner* — James W Rogers
(74) *Attorney, Agent, or Firm* — Hodgson Russ LLP

(57) ABSTRACT

The present invention is related to a mesoscale colloidal particle including a hydrophobe-rich core surrounded by hydrogen bonded outer shell. The outer shell includes water and at least one hydrotrope wherein the hydrotrope molecules form hydrogen bonds with water molecules. The invention is also related to an aqueous solution including at least one mesoscale colloidal particle as well as methods of making and using such mesoscale colloidal particles and their solutions.

8 Claims, 13 Drawing Sheets

(56) References Cited

OTHER PUBLICATIONS

Glew et al., "Aqueous non-electrolyte solutions: Part VII Water shell stabilization by interstitial nonelectrolytes," Hydrogen-Bonded Solvent Systems: Proceedings of a Symposium on Equilibria and Reaction Kinetics in Hydrogen-Bonded Solvent Systems, 1968, pp. 195-210.
Pang et al., "Order-disorder effects of small guests in clathrates studied by nuclear quadrupole resonance and crystallography. Part I. Carbon tetrachloride and related molecules in Ni(SCN)2(3-methylpyridine)4," Journal of Inclusion Phenomena and Molecular Recognition in Chemistry, 1992, vol. 13, pp. 63-76.
Mak et al., "Polyhedral clathrate hydrates. X. Structure of the double hydrate of tetrahydrofuran and hydrogen sulfide," The Journal of Chemical Physics, 1965, vol. 42, No. 8, pp. 2732-2737.
Ito et al., "A study of local structure formation in binary solutions of 2-butoxyethanol and water by Rayleigh scattering and Raman spectra," Bulletin of Chemical Society of Japan, 1983, vol. 56, No. 2, pp. 379-385.
Trent et al., "Propylene oxide," Kirk-Othmer Encyclopedia of Chemical Technology, John Wiley & Sons, Inc., 2001, 26 pages.
Davidson et al., "Chapter 3: Clathrate hydrates," In Franks F. (eds) Water in Crystalline Hydrates Aqueous Solutions of Simple Nonelectrolytes. Water (A comprehensive treatise), 1973, vol. 2, pp. 176-234.
Nishikawa et al., "Structural study of tert-butyl alcohol and water mixtures by X-ray diffraction," Journal of Physical Chemistry, 1990, vol. 94, pp. 6227-6231.
Bowron et al., "Structural investigation of solute-solute interactions in aqueous solutions of tertiary butanol," Journal of Physical Chemistry B, 1998, vol. 102, No. 18, pp. 3551-3563.
Mizuno et al., "Hydrophobic hydration of tert-butyl alcohol probed by NMR and IR," Journal of Molecular Liquids, 2000. vol. 85, pp. 139-152.
Vasquez et al., "Interfacial properties of tert-butyl alcohol solutions and their relation to clathrate formation," Journal of Physical Chemistry B, 2002, vol. 106, No. 10, pp. 2649-2655.
Fukasawa et al., "Molecular association in binary mixtures of tert-butyl alcohol-water and tetrahydrofuran-heavy water studied by mass spectrometry of clusters from liquid droplets," Journal of Physical Chemistry A, 2004, vol. 108, No. 1, pp. 59-63.
Paul et al., "Why tert-butyl alcohol associates in aqueous solution but trimethylamine-N-oxide does not," Journal of Physical Chemistry B, 2006, vol. 110, No. 21, pp. 10514-10518.
Malomuzh et al., "The cluster structure of dilute aqueous-alcoholic solutions and molecular light scattering in them," Russian Journal of Physical Chemistry A, 2007, vol. 81, No. 11, pp. 1777-1782.
Pradhan et al., "Structural transition in alcohol-water binary mixtures: A spectroscopic study," Journal of Chemical Sciences, 2008, vol. 120, No. 2, pp. 275-287.
Krivoglaz et al., "Fluctuon states of electrons," Soviet Physics Uspekhi, 1974, vol. 16, pp. 856-877.
Jacobson et al., "Amorphous precursors in the nucleation of clathrate hydrates," Journal of the American Chemical Society, 2010, vol. 132, pp. 11806-11811.
Anisimov et al., "Chapter 7: Thermodynamics of Fluids at Meso and Nano Scales," Applied Thermodynamics of Fluids, International Union of Pure and Applied Chemistry, 2010, pp. 172-214.
Chechko et al., "On the nature of relaxation processes in dilute water-glycerol solutions," Journal of Molecular Liquids, 2003, vol. 105, Nos. 2-3, pp. 211-214.
Mallamace et al., "Large supramolecular structures in water-alcohol mixtures evidenced by elastic light scattering," Il Nuovo Cimento D, 1992. vol. 14, No. 8, pp. 333-341.
Nabutovskii et al., "Charge density and order-parameter waves in liquid and solid electrolytes in the vicinity of the critical point," Physics Letters, 1980, vol. 79A, No. 1, pp. 98-100.
Sadakane et al., "Multilamellar structures induced by hydrophilic and hydrophobic ions added to a binary mixture of D2O and 3-methylpyridine," Physical Review Letters, 2009, vol. 103, pp. 167803-1-4.
Okamoto et al., "Precipitation in aqueous mixtures with addition of a strongly hydrophilic or hydrophobic solute," Physical Review E, 2010, vol. 82, pp. 051501-1-20.
Onuki et al., "Phase transitions in soft matter induced by selective salvation," Bulletin of the Chemical Society of Japan, 2011, vol. 84, No. 6, pp. 569-587.
Kusalik et al., "Computer simulation study of tert-butyl alcohol. 2. Structure in aqueous solution," Journal of Physical Chemistry B, 2000, vol. 104, No. 40, pp. 9533-9539.
Subramanian et al., "Mesoscale inhomogeneities in aqueous solutions of 3-methylpyridne and tertiary butyl alcohol," Journal of Chemical & Engineering Data, 2011, vol. 56, pp. 1238-1248.
Franks et al., "The structural properties of alcohol-water mixtures," Quarterly Reviews Chemical Society, 1966, vol. 20, 44 pages.
Darrigo et al., "Small-angle neutron scattering study of D2O-alcohol solutions," Journal of the Chemical Society, Faraday Transactions, 1990, vol. 86, pp. 1503-1509.
Darrigo et al., "Temperature and concentration dependence of SANS spectra of aqueous solutions of short-chain amphiphiles," The European Physical Journal E., 2009, vol. 29, pp. 37-43.
Misawa et al., "A visualized analysis of small-angle neutron scattering intensity: Concentration fluctuation in alcohol-water mixtures," Journal of Applied Crystallography, 2007, vol. 40, pp. s93-s96.
Koehler et al., "The Lifshitz line in binary systems: Structures in water/C4E1 mixtures," The Journal of Chemical Physics, 1994, vol. 101, pp. 10843-10849.
Yoshida et al., "Concentration fluctuations and cluster dynamics of 2-butoxyethanol-water mixtures by small-angle neutron scattering and neutron spin echo techniques," Journal of Molecular Liquids, 2005, vol. 119, pp. 125-131.
Finney et al., "The structure of aqueous solutions of tertiary butanol," Journal of Physics: Condensed Matter, 2000, vol. 12, pp. A123-128.
Bowron et al., "Structural investigation of solute-solute interactions in aqueous solutions of tertiary butanol," Journal of Physical Chemistry B. 1998, vol. 102, pp. 3551-3563.
Finney et al., "Molecular and mesoscale structures in hydrophobically driven aqueous solutions," Biophysical Chemistry, 2003, vol. 105, pp. 391-409.
Bowron et al., "Structural characteristics of a 0.23 mole fraction aqueous solution of tetrahydrofuran at 25° C," Journal of Physical Chemistry B, 2006, vol. 110, pp. 20235-20245.
Harris et al., "Diffusion and structure in water-alcohol mixtures: Water + tert-butyl alcohol (2-methyl-2-propanol)," Journal of Physical Chemistry A, 1999, vol. 103, pp. 6508-6513.
Nishi et al., "Hydrogen bonding cluster formation and hydrophobic solute association in aqueous solution of ethanol," Journal of Physical Chemistry, 1995, vol. 99, pp. 462-468.
Kusalik et al., "Computer simulation study of tert-butyl alcohol. 2. Structure in aqueous solution," Journal of Physical Chemistry B, 2000, vol. 104, pp. 9526-9532.
Guo et al., "Molecular structure of alcohol-water mixtures," Physical Reviews Letters, 2003, vol. 91, No. 15, pp. 157401-1-4.
Fornili et al., "Molecular dynamics simulation of aqueous solutions of trimethylamine-N-oxide and tert-butyl alcohol," Physical Chemistry Chemical Physics, 2003, vol. 5, pp. 4905-4910.
Kiselev et al., "The study of hydrophobicity in water-methanol and water-tert-butanol mixtures," Journal of Molecular Liquids, 2004, vol. 110, pp. 193-199.
Roney et al., "A molecular dynamics study of the aggregation phenomena in aqueous n-propanol," Journal of Physical Chemistry B, 2004, vol. 108, pp. 7389-7401.
Allison et al., Clustering and microimmiscibility in alcohol-water mixtures: Evidence from molecular-dynamics simulations, Physical Review B, 2005, vol. 71, pp. 024201-1-5.
Kezic et al., "Aqueous tert-butanol mixtures: A model for molecular emulsions," The Journal of Chemical Physics, 2012, vol. 137, pp. 014501-1-12.

(56) References Cited

OTHER PUBLICATIONS

Gupta et al., "Aggregation in dilute aqueous tert-butyl alcohol solutions: Insights from large-scale simulations," The Journal of Chemical Physics, 2012, vol. 137, pp. 034509-1-12.
Li et al., "Large-scale structures in tetrahydrofuran-water mixture with a trace amount of antioxidant butylhydroxytoluene (BHT)," The Journal of Physical Chemistry B, 2011, vol. 115, pp. 7887-7895.
Vuks et al., "The scattering of light and phase transition in solutions of tertiary butyl alcohol in water," Optics Communications, 1972, vol. 5, No. 4, pp. 277-278.
Beer et al., "Comments on 'The scattering of light and phase transition in solutions of tertiary butyl alcohol in water,'" Optics Communications, 1974, vol. 11, No. 2, pp. 150-151.
Iwasaki et al., "Light scattering study of clathrate hydrate formation in binary mixtures of tert-butyl alcohol and water," The Journal of Physical Chemistry, 1977, vol. 81, No. 20, pp. 1908-1912.
Iwasaki et al., "Light-scattering study of clathrate hydrate formation in binary mixtures of tert-butyl alcohol and water. 2. Temperature effect," The Journal of Physical Chemistry, 1979, vol. 83, No. 4, pp. 463-468.
Euliss et al., "Dynamic light scattering studies of concentration fluctuations in aqueous t-butyl alcohol solutions," The Journal of Chemical Physics, 1984, vol. 80, pp. 4767-4773.
Bender et al., "A dynamic light scattering study of the tert-butyl alcohol-water system," The Journal of Physical Chemistry, 1986, vol. 90, No. 8, pp. 1700-1706.
Bender et al., "Dynamic light scattering measurements of mutual diffusion coefficients of water-rich 2-butoxyethanol/water systems," The Journal of Physical Chemistry, 1988, vol. 92, No. 6, pp. 1675-1677.
Georgalis, "Cluster formation in aqueous electrolyte solutions observed by dynamic light scattering," The Journal of Physical Chemistry B, 2000, vol. 104, No. 15, pp. 3405-3406.
Yang et al., "Laser light-scattering study of solution dynamics of water/cycloether mixtures," The Journal of Physical Chemistry B, 2004, vol. 108, No. 31, pp. 11866-11870.
Sedlak et al., "Large-scale supramolecular structure in solutions of low molar mass compounds and mixtures of liquids: I. Light scattering characterization," The Journal of Physical Chemistry B, 2006, vol. 110, No. 9, pp. 4329-4338.
Sedlak et al., "Large-scale supramolecular structure in solutions of low molar mass compounds and mixtures of liquids: II. Kinetics of the formation and long-time stability," The Journal of Physical Chemistry B, 2006, vol. 110, No. 9, pp. 4339-4345.
Sedlak et al., "Large-scale supramolecular structure in solutions of low molar mass compounds and mixtures of liquids. III. Correlation with molecular properties and interactions," The Journal of Physical Chemistry B, 2006, vol. 110, No. 28, pp. 13976-13984.
Jin et al., "Observation of kinetic and structural scalings during slow coalescence of nanobubbles in an aqueous solution," The Journal of Physical Chemistry B Letters, 2007, vol. 111, pp. 13143-13146.
Kostko et al., "Criticality in aqueous solutions of 3-methylpyridine and sodium bromide," Physical Review E, 2004, vol. 70, pp. 026118-1-11.
Subramanian et al., "Resolving the mystery of aqueous solutions of tertiary butyl alcohol," The Journal of Physical Chemistry B, 2011, vol. 115, pp. 9179-9183.
Subramanian, "Self-Assembly in Aqueous Solutions of a Non-Ionic Hydrotrope," Doctor of Philosophy Dissertation, University of Maryland, College Park, 2012, 173 pages.
Srinivas et al., "When does the switch from hydrotropy to micellar behavior occur?," Langmuir, 1998, vol. 14, pp. 6658-6661.
Hodgdon et al., "Hydrotropic solutions," Current Opinion in Colloid & Interface Science, 2007, vol. 12, pp. 121-128.
Eastoe et al., "Action of hydrotropes and alkyl-hydrotropes," Soft Matter, 2011, vol. 7, pp. 5917-5925.
Subramanian et al., "Thermodynamic anomalies and structural fluctuations in aqueous solutions of tertiary butyl alcohol," Herald of St. Petersburg University (Vestnik), 2013, vol. 4, pp. 139-153.
Ott et al., "(Solid+liquid) phase equilibria and solid-hydrate formation in water + methyl, + ethyl, + isopropyl, and + tertiary butyl alcohols," The Journal of Chemical Thermodynamics, 1979, vol. 11, No. 8, pp. 739-746.
Nishikawa et al., "Structural study of tert-butyl alcohol and water mixtures by X-ray diffraction," The Journal of Physical Chemistry, 1990, vol. 94, No. 16, pp. 6227-6231.
Tanaka et al., "Clathrate-like structure of water around some nonelectrolytes in dilute solution as revealed by computer simulation and X-ray diffraction studies," The Journal of Inclusion Phenomena, 1984, vol. 2, pp. 119-126.
Jacob et al., "Novel phase-transition behavior near liquid/liquid critical points of aqueous solutions: Formation of a third phase at the interface," Physical Chemistry Chemical Physics, 2001, vol. 3, pp. 829-831.
Horn et al., "Development of an improved four-site water model for biomolecular simulations: TIP4P-Ew," The Journal of Chemical Physics, 2004, vol. 120, No. 20, pp. 9665-9678.
Vanommeslaeghe et al., "CHARMM General Force Field (CGenFF): A force field for drug-like molecules compatible with the CHARMM all-atom additive biological force fields," Journal of Computational Chemistry, 2010, vol. 31, No. 4, pp. 671-690.
Martinez et al., "PACKMOL: A package for building initial configurations for molecular dynamics simulations," Journal of Computational Chemistry, 2009, vol. 30, No. 13, pp. 2157-2164.
Phillips et al., "Scalable molecular dynamics with NAMD," Journal of Computational Chemistry, 2005, vol. 26, No. 16, pp. 1781-1802.
Darden et al., "Particle Mesh Ewald: an N-Log(N) Method for Ewald Sums in Large Systems," The Journal of Chemical Physics, 1993, vol. 98, No. 12, pp. 10089-10092.

* cited by examiner

Figure 8B:
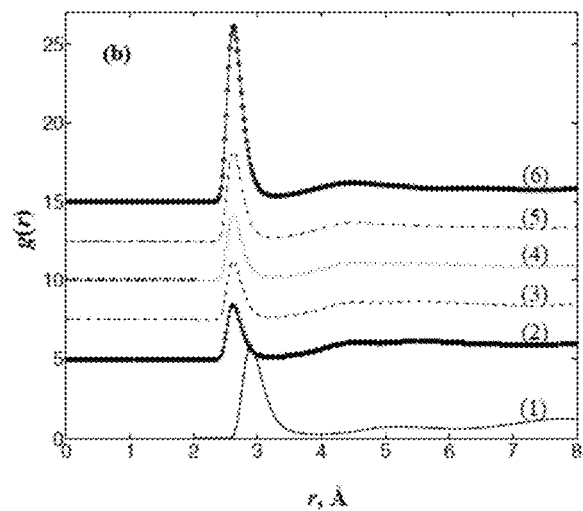
Figure 9A-E:
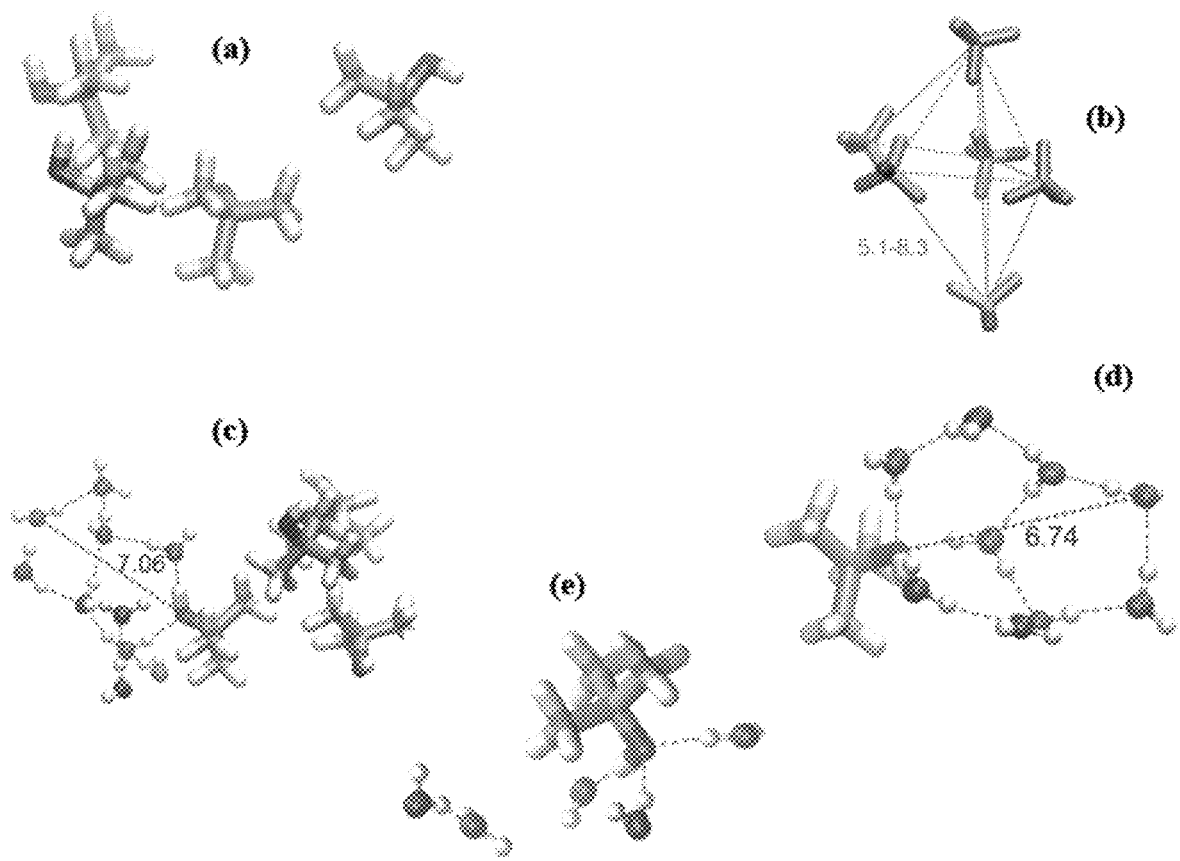

HIGHLY STABLE COLLOID FROM AQUEOUS SOLUTIONS OF SMALL ORGANIC MOLECULES

CROSS REFERENCE TO RELATED PATENT APPLICATION

This application claims the benefit of U.S. Provisional Patent Application Ser. No. 61/649,755, filed May 21, 2012, which is hereby incorporated by reference in its entirety.

The subject matter of this application was made with support from United States Government under Grant Number CHE-1012052 awarded by the National Science Foundation. The U.S. government has certain rights in the invention.

FIELD OF THE INVENTION

The present invention in related in general to mesoscale colloidal particles, a solution containing such mesoscale colloidal particles, and methods for preparation and use of such mesoscale colloidal particles.

BACKGROUND OF THE INVENTION

Solubility is one of the most important physicochemical properties for development of liquid products. Often there is a need for solubilization systems that are suitable for solubilizing poorly soluble chemical compounds.

Many drugs and drug candidates are poorly water-soluble, which limits their clinical applications. Increasing numbers of newly developed drugs are poorly water-soluble and such poor water-solubility causes significant problems in producing formulations of a sufficiently high bioavailability with reproducible effects.

The poor bioavailability of poorly water-soluble drugs becomes even worse when the drug is given orally. Since oral administration is the most convenient method of delivering drugs and is used for the majority of drugs, developing a method for increasing the water-solubility of poorly soluble drugs is highly important. Increasing the water-solubility of poorly water-soluble drugs should allow development of effective dosage forms.

In order to overcome solubility constraints, many solution based products such as paints, detergents, pastes and the like are formulated as colloidal dispersions of solid particles or liquid droplets in a liquid media. These products, if 'not stirred before use', tend to form two layers in the container—the bottom layer with the heavier phase, and the top layer with the lighter phase. In order to avoid such a separation of the layers and have a stable product, colloidal dispersions need to be stabilized. Traditionally colloidal dispersions are stabilized by electrostatic stabilization or by the addition of surfactants. More recently, polymers are also used for the same purpose. However, addition of additives like charged particles, polymers and surfactants is not always feasible or desirable. Furthermore, in order to make colloidal dispersions expensive solubilization processes must be used. For example, micronization is often used for preparing formulations of hydrophobic drugs. Micronization involves milling, bashing or grinding poorly soluble compounds. Such methods often involve use of expensive instruments and are time consuming.

The present invention is directed to overcoming these and other deficiencies in the art.

SUMMARY OF THE INVENTION

A first aspect of the present invention is generally related to a mesoscale colloidal particle including a hydrophobe-rich core surrounded by hydrogen bonded outer shell. The outer shell includes water and at least one hydrotrope wherein the hydrotrope molecules form hydrogen bonds with water molecules.

In a second aspect, the present invention is related to an aqueous solution including at least one mesoscale colloidal particle as described in the first aspect of the present invention.

In a third aspect, the present invention is related to a method of making a solution which includes such mesoscale colloidal particles. The method includes adding water, at least one hydrotrope, and a hydrophobic organic molecule to form a mixture and allowing the mixture to form an aqueous solution including at least one mesoscale colloidal particle according to the first aspect of the present invention.

Hydrotropy is a molecular phenomenon whereby adding a second solute (the hydrotrope) results in an increase in the aqueous solubility of poorly soluble solutes. Solubility enhancement is one of the advantages of hydrotropes. There are multiple uses and applications of the present invention which take advantage of a hydrotrope's unique properties such as its amphiphilic nature, hydrogen-bonding ability, and specific interactions with solutes and solvent. Due to their specific solubilizing properties, hydrotropes could be used in a wide variety of industries. For example, in pharmaceutical industry, hydrotropes can be used to transport hydrophobic drugs in aqueous media and to enhance the dissolution and permeation of drugs in biological systems. Such formulations can be used for transdermal, oral, or transmucosal drug delivery.

In soap and detergent industry, hydrotropes could be used to "solubilize" surfactants and make products with concentrated amounts of surfactants. In food and drug industry, hydrotropes could be used for making products such as pastes, syrups and the like or in paint industry for making products such as paints, enamel and the like. Hydrotropes can also be used as co-solvents in detergent, drug, agrochemicals, or cosmetic formulations along with surfactants to enhance or inhibit micelle formation.

Hydrotropes could be used as catalysts in heterogeneous chemical reactions to enhance reaction rates, in the separation of mixtures by selective extraction, as agents used to alter the thermodynamic behavior of liquid crystalline phases, and as molecular probes to determine properties of the microenvironment. Certain hydrotropes, such as proline, are protein compatible, and help in maintaining cellular osmosis.

The fast process corresponds to molecular diffusion with a diffusion coefficient of $1.2 \times 10^{-6}$ cm$^2$/sec and a hydrodynamic radius of 0.8 nm. The slow process, which is termed as mesoscale solubilization, corresponds to long-lived, highly stable mesoscopic droplets of about 200 nm in size, with an average diffusion coefficient of $4.1 \times 10^{-9}$ cm$^2$/sec.

Figure 3A:
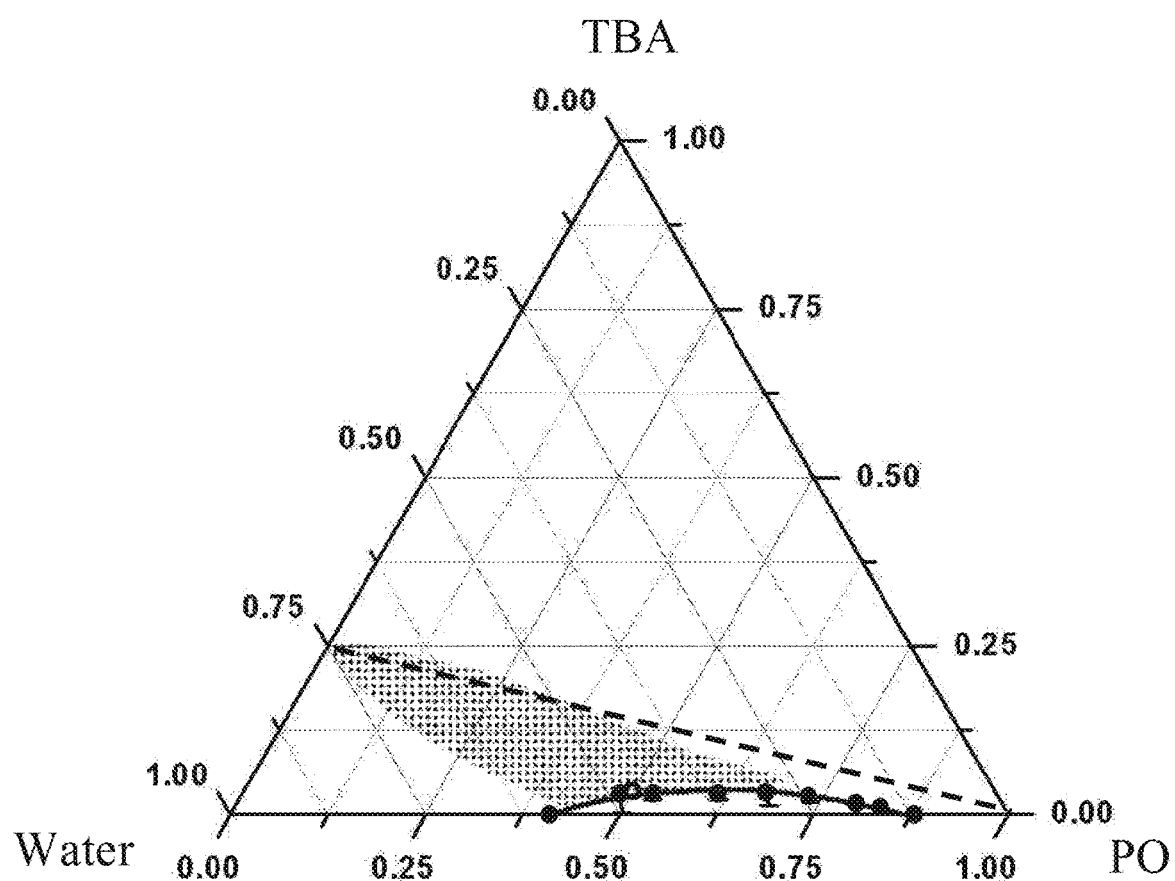
Figure 3B:
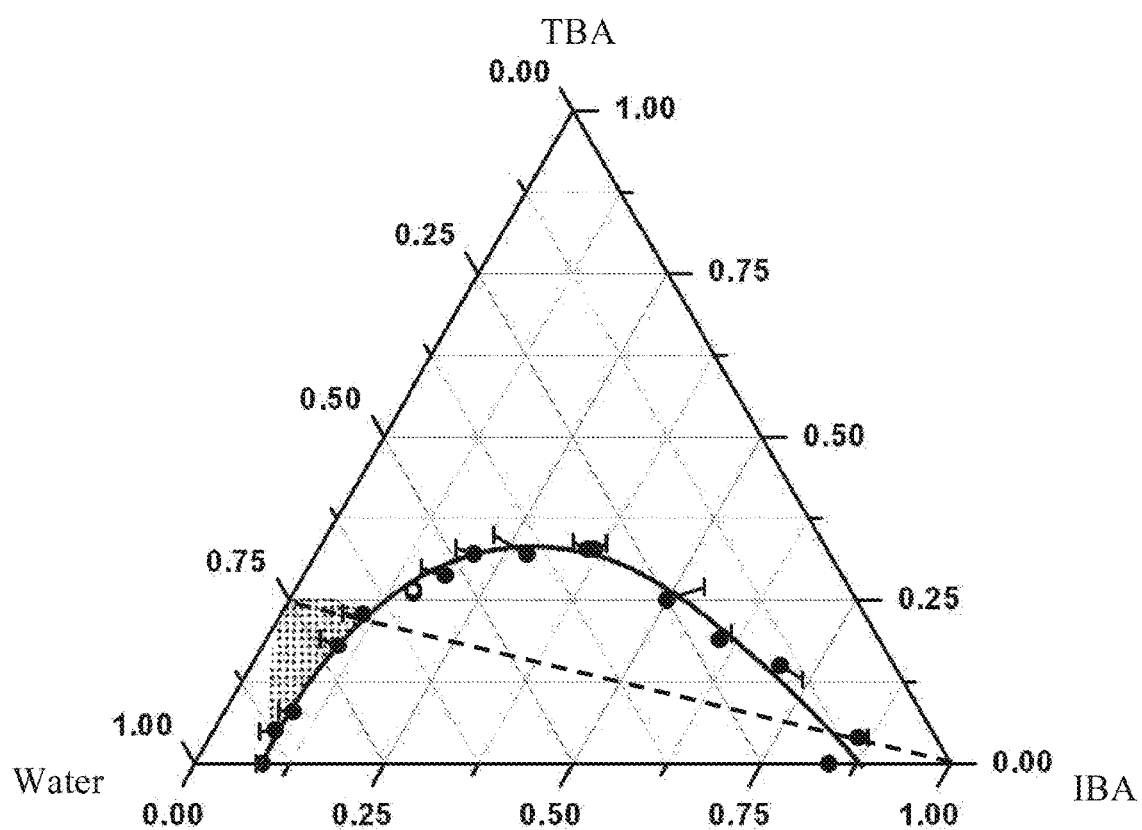
Figure 3C:
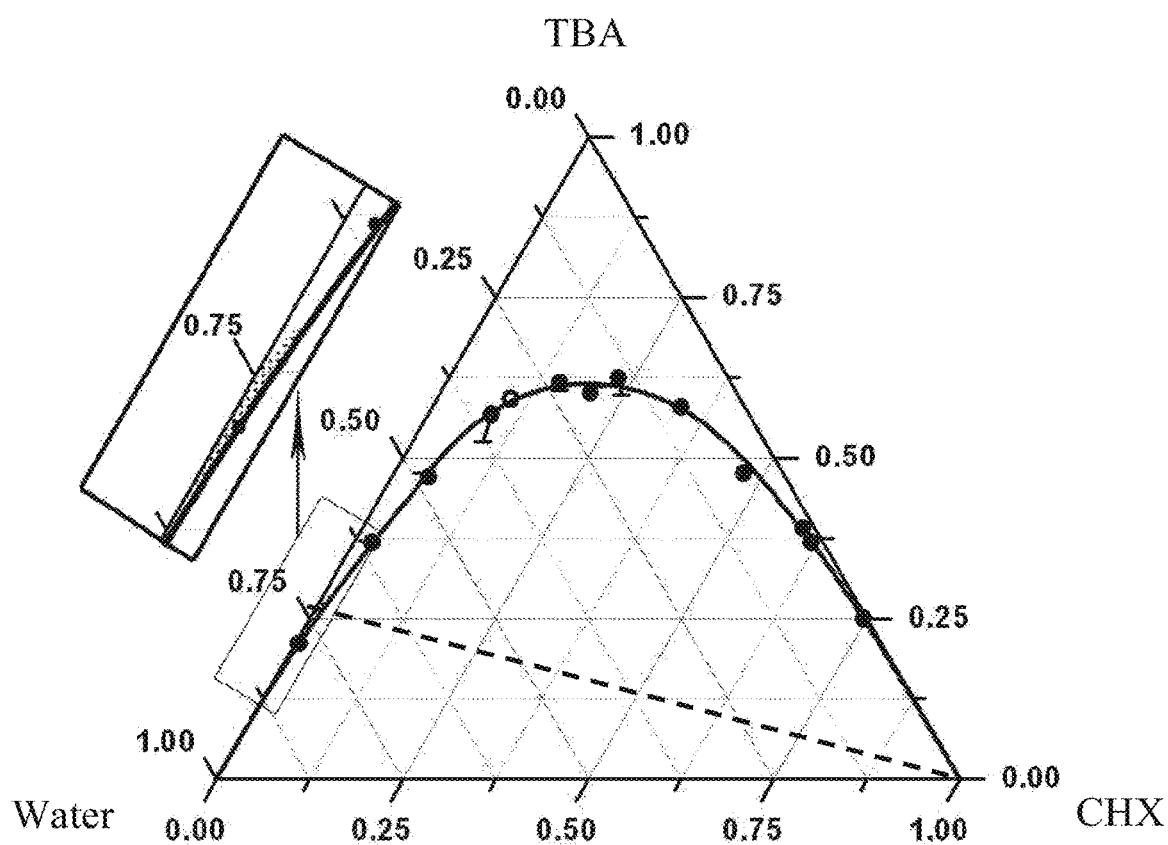

FIGS. 3A-C shows ternary phase diagrams of TBA-water-hydrophobe systems at ambient conditions. All concentrations are in mass fractions. The smooth line across the points is a guide to the eye. Open circles represent approximate location of the critical point. The dashed line from the vertex of the hydrophobe represents concentrations with a constant TBA-Water ratio (25:75 mass basis/7:93 mole basis) where thermodynamic anomalies in the binary TBA-water solution exhibit extrema. The dotted area in the phase diagram shows the region where mesoscopic droplets are observed. FIG. 3A shows TBA-Water-Propylene Oxide (PO) phase diagram (T≅25° C.). FIG. 3B shows TBA-Water-Isobutyl Alcohol (IBA) phase diagram (T≅21° C.). FIG. 3C shows TBA-Water-CHX phase diagram (T≅21° C.). The smooth line across the points is a guide to the eye. All concentrations are shown as mass fractions. Open circle (CP) represents approximate location of the critical point. The dashed line from the vertex of the hydrophobe (CHX) represents concentrations with a constant TBA-water ratio (25:75 mass basis/7:93 mole basis) where thermodynamic anomalies in the binary TBA-water solution are observed. The region inside solid curve is the two-phase region, while the region outside this curve is the macroscopic one-phase region. The dotted area in the phase diagram shows the region where mesoscopic droplets are observed.

Figure 4:
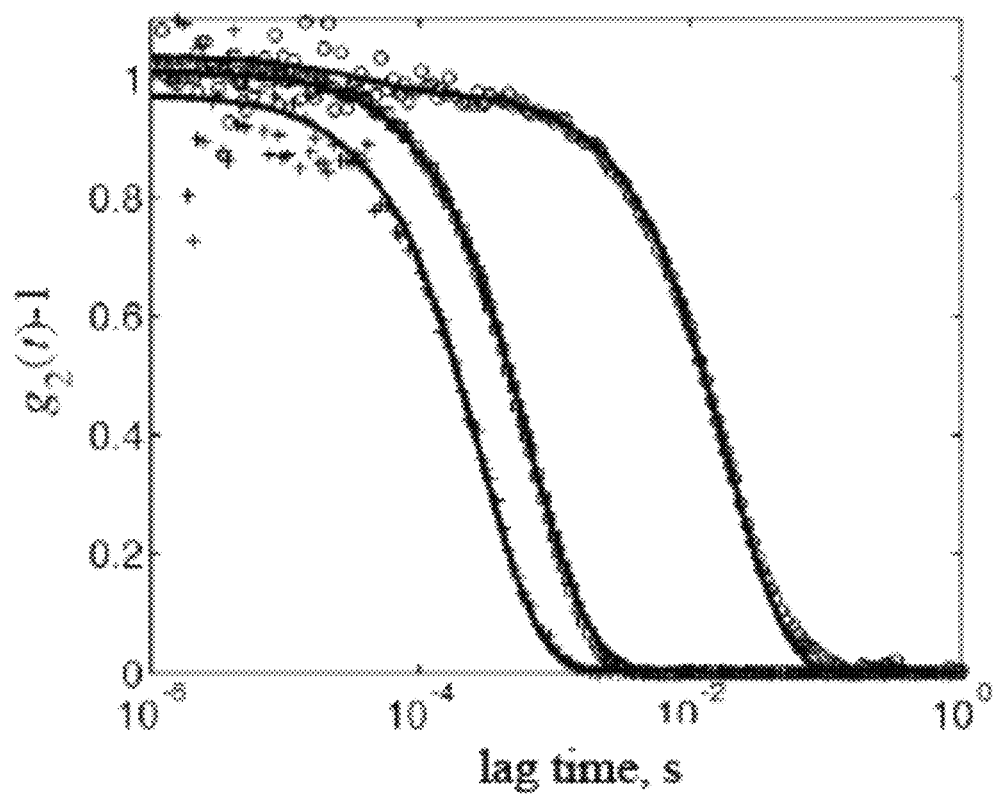

FIG. 4 shows intensity auto-correlation functions for TBA-water-IBA solutions at T=10° C. and a scattering angle of θ=45°. Sample concentrations are displayed in Table 1. Squares (sample #A) and crosses (sample #B) represent solutions that are close to the critical point of the system, indicating a relaxation time of about 1.3 ms and 0.6 ms, respectively. These correspond to correlation lengths of 5 nm and 2 nm, respectively. The circles correspond to sample C from Table 1, which additionally show the presence of mesoscopic droplets. The droplets have a relaxation time of about 37 ms, which corresponds to a length scale of about 130 nm.

Figure 5:
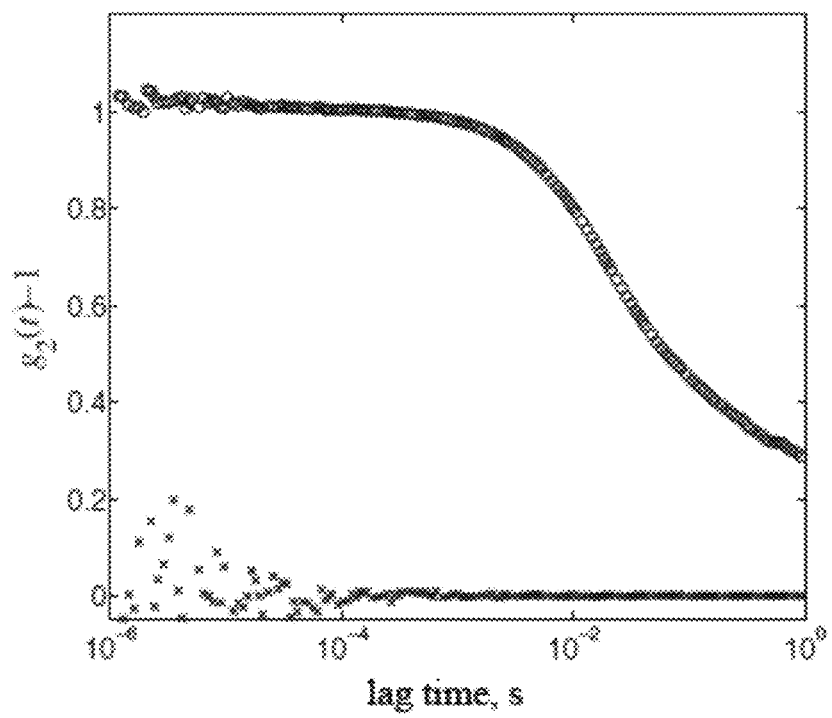

FIG. 5 shows intensity auto-correlation functions for a TBA-water-CHX system in the two-phase region measured after ~3 days of preparation (T=25° C. and scattering angle θ=45°). Overall sample concentration is 0.13 mass fraction CHX and 0.29 mass fraction TBA. Correlation function from the aqueous phase (circles) shows the presence of mesoscopic droplets, while the correlation function from the CHX rich phase (crosses) shows no such phenomenon. When measured after a period of 3 months, the aqueous phase and the CHX rich phase show no correlations, thus indicating that in a two-phase system, the mesoscopic droplets phase separate, albeit very slowly.

Figure 6:

FIG. 6 shows an image of TBA-water-CHX system in the two-phase region. The vial diameter is 2.5 cm. The overall concentration of the sample is 0.16 mass fraction CHX and 0.40 mass fraction TBA. The sample shows the presence of a novel phase at the interface of the aqueous rich and CHX rich layers.

Figure 7:
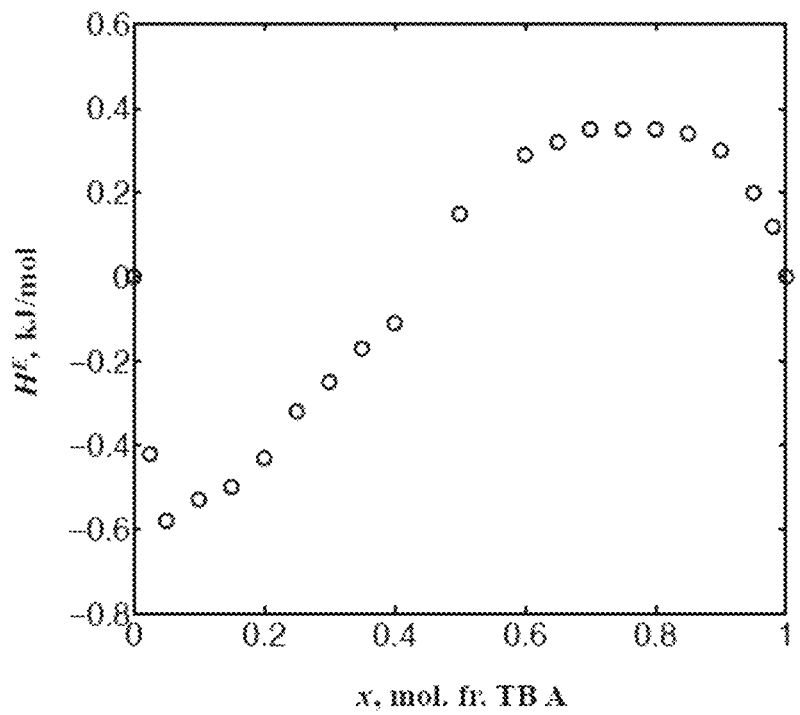

FIG. 7 shows excess enthalpy (heat of mixing) of aqueous TBA solutions at T=25° C. (reproduced from Koga, *Can. J. Chem.*, 1986, 64, 206-207, which is hereby incorporated by reference in its entirety). The negative values of the excess enthalpy in the water rich region indicate favorable solute-solvent interactions.

Figure 8A:
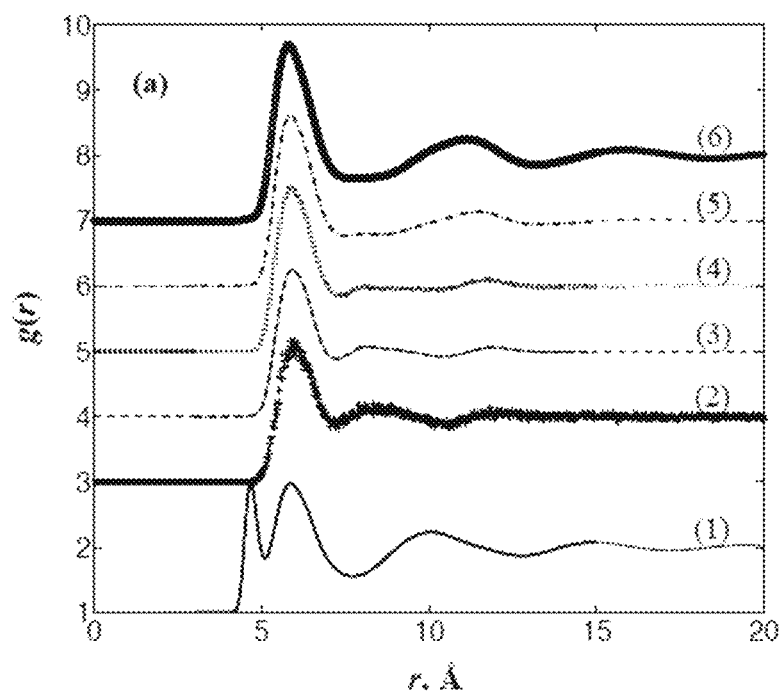

FIG. 8 shows radial distribution functions between central carbons of TBA (FIG. 8A) and oxygen of TBA and oxygen of water (for pure TBA RDF is between oxygen atoms of TBA) (FIG. 8B). The curves are offset vertically for clarity. (1) corresponds to pure TBA; (2) corresponds to 1 mol % (4 mass %) TBA; (3) corresponds to 4 mol % (15 mass %) TBA; (4) corresponds to 7 mol % (24 mass %) TBA; (5) corresponds to 18 mol % (47 mass %) TBA; and (6) corresponds to 40 mol % (73 mass %) TBA.

FIG. 9 shows snapshots from MD simulations in aqueous solutions of TBA with increasing concentration of TBA. TBA molecules are represented by licorice model, while water molecules are represented by ball and stick model. The structure between TBA and water is fairly similar from 1 to 7 mol % TBA. The only difference is the amount and size of TBA clusters with increasing TBA concentration. However, beyond ~7 mol % TBA, the clusters do not seem to be well-defined and loose their structural integrity. FIG. 9A shows 1 mol (4 mass %) TBA; FIG. 9B shows 4 mol % (15 mass %) TBA; FIG. 9C shows 7 mol % (24 mass %) TBA; FIG. 9D shows 18 mol % (47 mass %) TBA; and FIG. 9E shows 40 mol % (73 mass %) TBA.

Figure 10A:
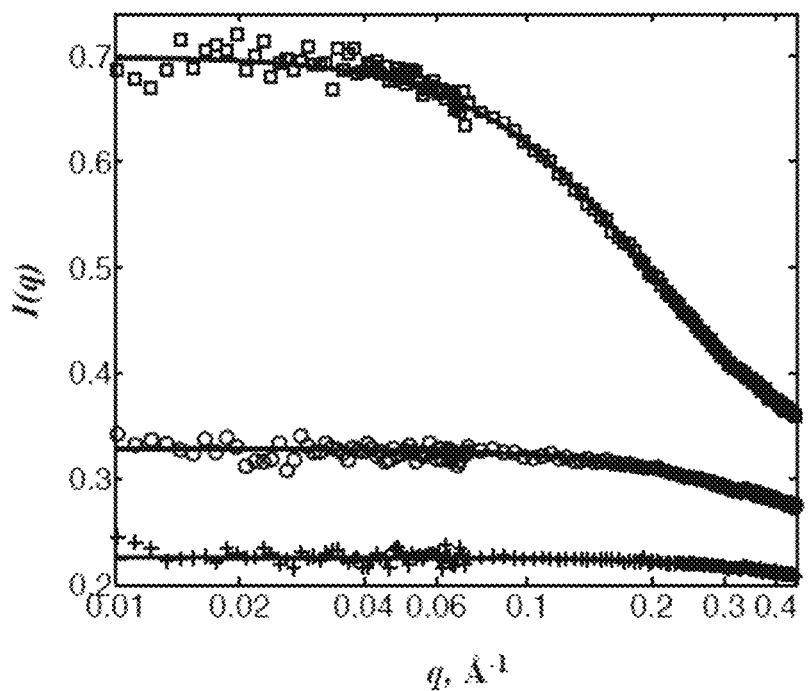
Figure 10B:
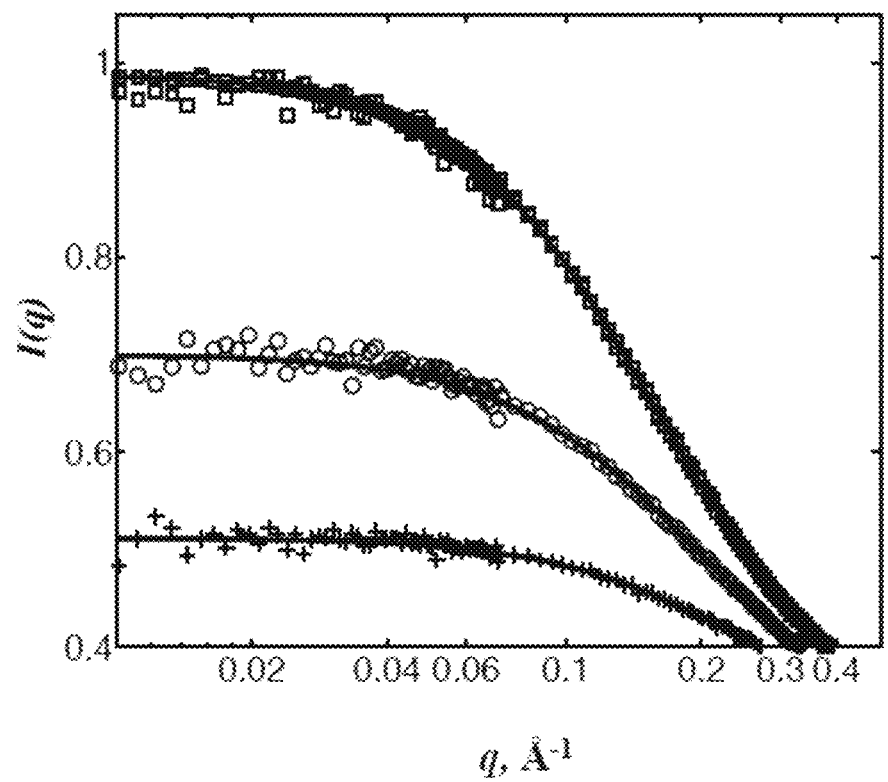

FIG. 10A shows SANS data from TBA-heavy water solutions at T=25° C. Crosses: 3.5 mol % (12 mass %) TBA (sample #SB1). Circles: 5 mol % (16 mass %) TBA (sample #SB2). Squares: 7.4 mol % (23 mass %) TBA (sample #SB3). Statistical error bars are comparable to the size of the symbols. The solid lines are fits to the data in accordance with Eq. (8). The results of the fits are summarized in Table 3. FIG. 10B shows SANS data from a 7.4 mol % (23 mass %) TBA-heavy water solution (sample #SB3). Crosses: 10° C. Circles: 25° C. Squares: 40° C. Statistical error bars are comparable to the size of the symbols. The black lines are fits to the data in accordance with Eq. (8). The results of the fits are summarized in Table 3.

Figure 11:
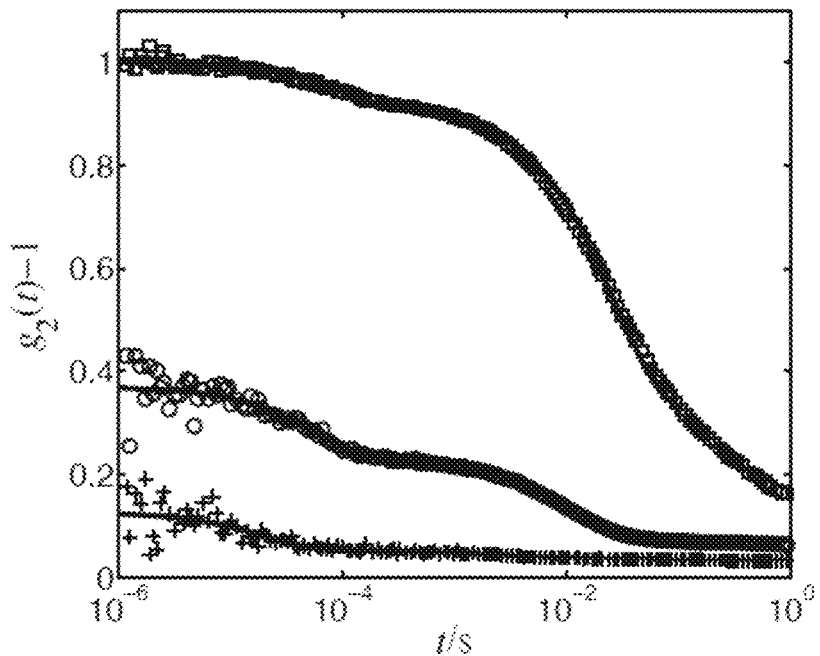

FIG. 11 shows time-dependent intensity autocorrelation functions obtained in aqueous solutions of TBA from dynamic light scattering (θ=45°). The solid lines are fits to the data in accordance with Eq. (4). Circles represent the correlation function obtained in ~8 mol % (26 mass %) TBA solution (TBA procured from Sigma Aldrich) at T=24° C. This correlation function shows the presence of two relaxation modes—the fast mode with a relaxation time of ~65 μs and a slow mode with a relaxation time of ~22 ms. After filtering this solution multiple times with a 20 nm Anopore filter at ~10° C., the slow mode is almost eliminated (correlation function represented by crosses). Adding trace amounts of a hydrophobic component (0.03 mol % cyclohexane) regenerates the slow mode (correlation function represented by squares). Statistical error bars are comparable to the size of the symbols.

Figure 12:
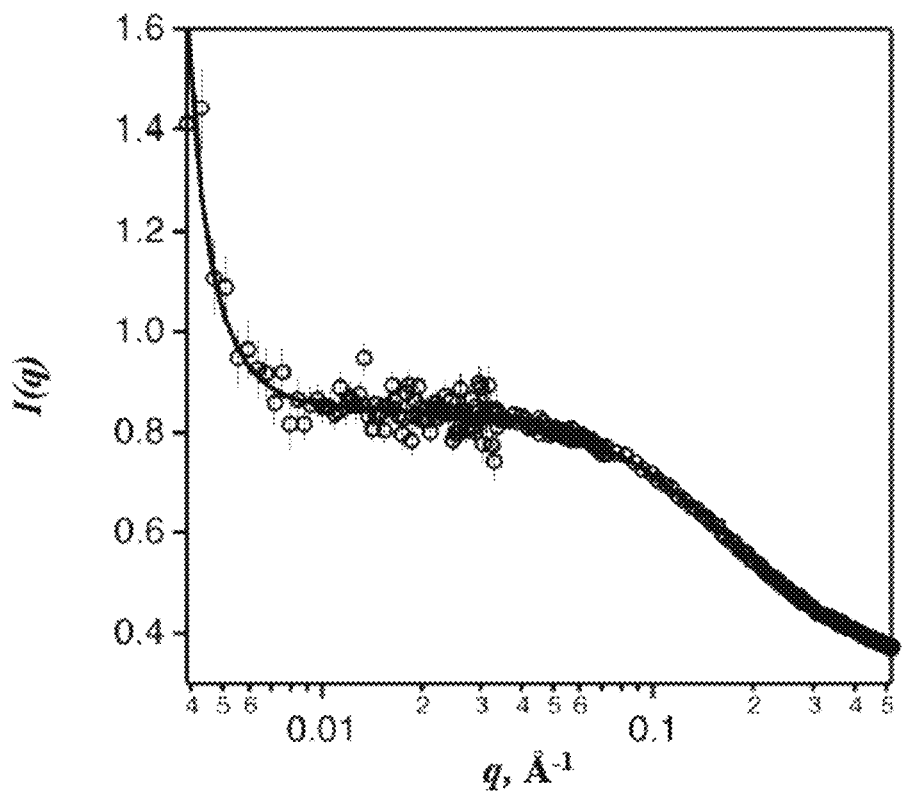

FIG. 12 shows SANS data from a TBA-heavy water-CHX solution at T=25° C. 7.4 mol % TBA (23 mass %), 0.03 mol % (0.1 mass %) CHX (sample #ST1 from Table 2). The black line is a fit to the data in accordance with Eq. (8). The results of the fit are summarized in Table 3.

Figure 13:
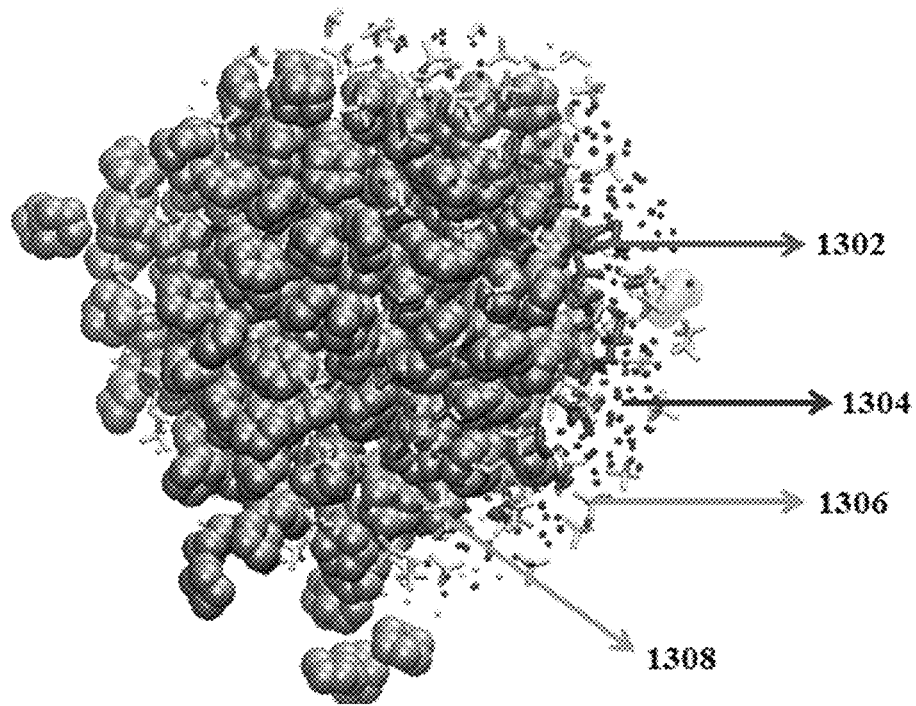

FIG. 13 shows snapshots (at ~50 ns) from MD simulations of a TBA-water-CHX solution (sample #T1 from Table 2). TBA molecules are represented by licorice model, while van der Waals spheres represent CHX molecules. This snapshot demonstrates the formation of a "droplet" with aggregated CHX molecules in the core, surrounded by primary and secondary layers of TBA molecules. These layers are further solvated by a water layer and a tertiary layer of TBA molecules. Element 1302 shows the primary and the secondary layers of TBA molecules, element 1304 represents a layer of water molecules, element 1306 shows tertiary and higher order layers of TBA molecules, and element 1308 shows CHX molecules.

Figure 14A:
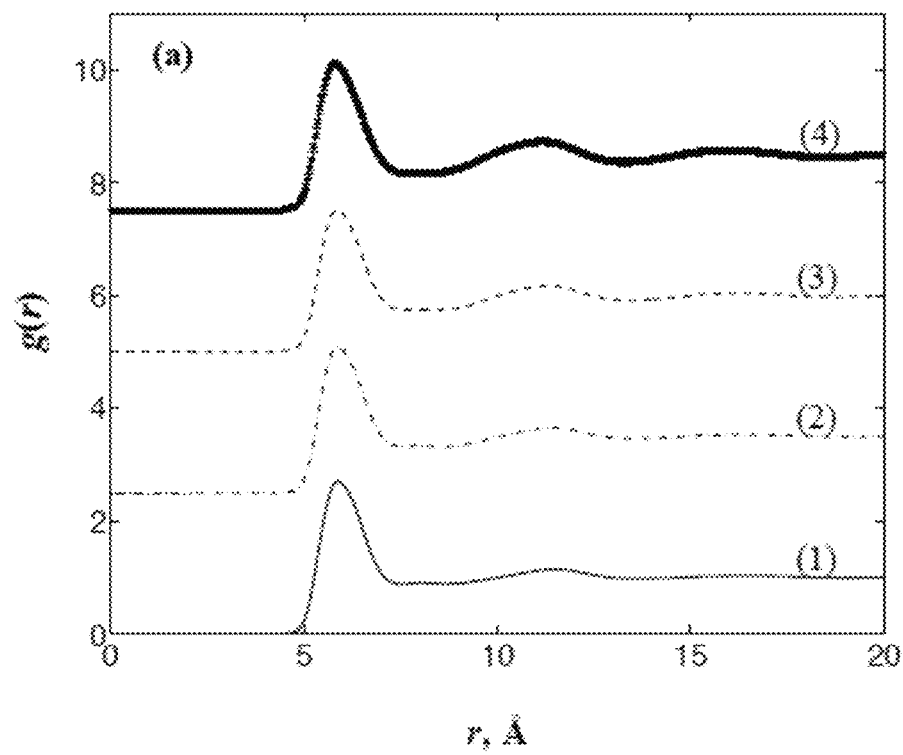
Figure 14B:
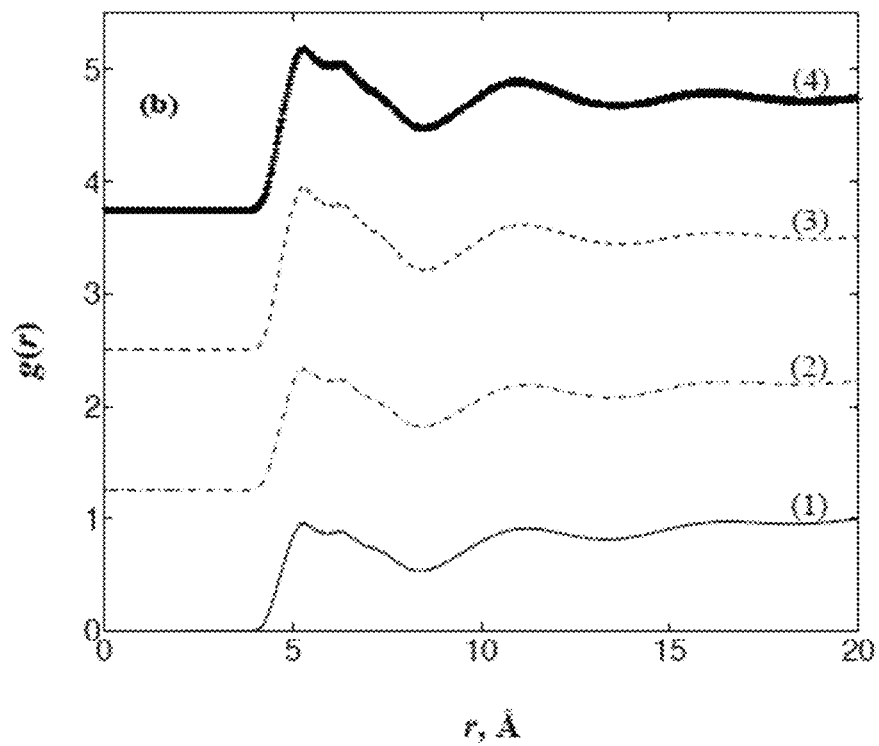

FIG. 14 shows radial distribution functions in TBA-water-CHX solutions with increasing concentrations of TBA (samples T1 to T4 from Table 2). FIG. 14A relates to RDFs between central C atoms of TBA. FIG. 14B shows RDFs between central C of TBA and C1 on CHX.

Figure 15:
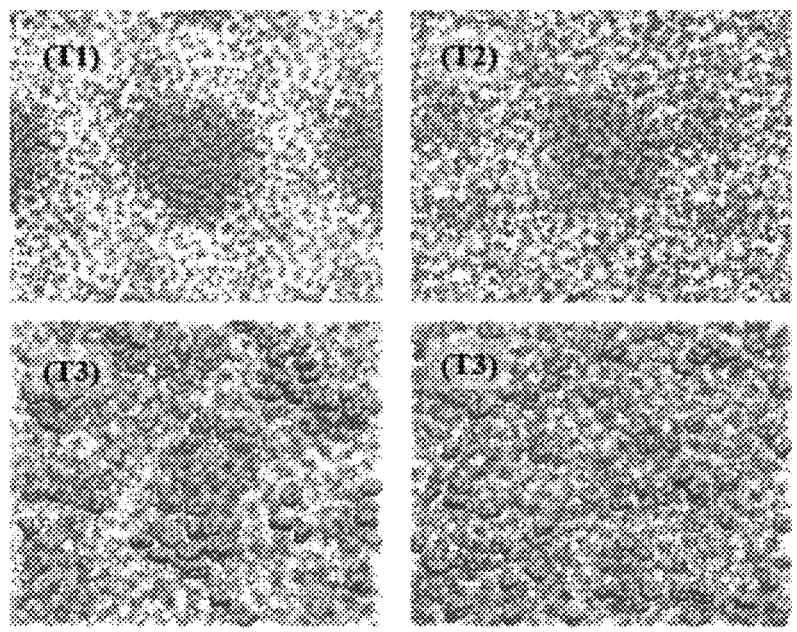

FIG. 15 shows snapshots from MD simulations in TBA-water-CHX system with increasing concentrations of TBA (samples #T1 to T4 from Table 2). These snapshots indicate that as the TBA concentration increases, the tendency of CHX to form droplets decreases. At high TBA concentrations, TBA and CHX preferred to remain mixed, rather than form the droplets.

Figure 16:
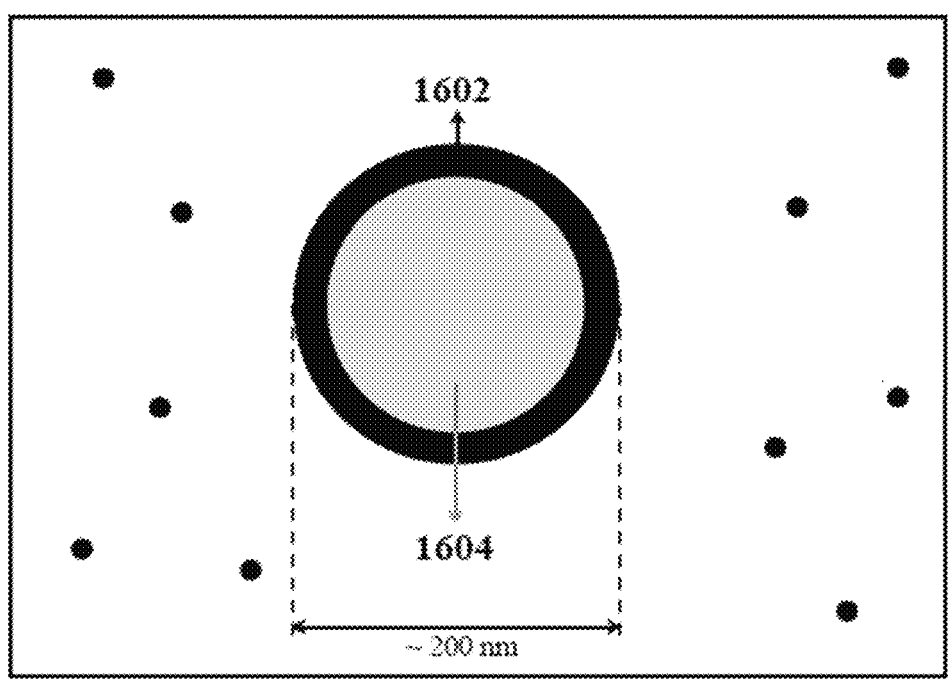

FIG. 16 shows schematic representation of meso scale solubilization in aqueous solutions of hydrotropes containing a hydrophobe. The mesoscopic droplets have a hydrophobic core surrounded by a hydrogen-bonded microemulsion-like hydrotrope-water outer shell. Element 1602 shows the hydrotrope-water shell and element 1604 shows the hydrophobic core.

DETAILED DESCRIPTION OF THE INVENTION

In a first aspect, the present invention is related to mesoscale colloidal particles. These particles include a hydrophobe-rich core surrounded by hydrogen bonded outer shell. The outer shell includes water and at least one hydrotrope wherein the hydrotrope molecules form hydrogen bonds with water molecules.

Binary solutions including hydrotrope and water form short-lived (<1 nm in size), short-ranged (lifetime of tens of picoseconds) micelle-like structural fluctuations (Subramanian et al., *Вестник СПбГу* (Herald of St. Petersburg University), 2013, 4, 140-153, which is hereby incorporated by reference in its entirety). These structural fluctuations seem to be responsible for the anomalies in the thermodynamic properties of aqueous TBA solutions.

Mesoscale colloidal particles or droplets of the present invention occur in aqueous solutions of hydrotropes when the solution contains a third, more hydrophobic, component. The particles exist in ternary systems only in the concentration range where structural fluctuations and thermodynamic anomalies are observed in the binary water-hydrotrope solutions.

Addition of a hydrophobe seems to stabilize the structural fluctuations occurring in hydrotrope-water, and leads to the formation of larger mesoscopic particles of about 100 nm in size. The structure of these mesoscopic particles is such that they have a hydrophobe-rich core, surrounded by a hydrogen-bonded shell of water and hydrotrope molecules. These particles can be extremely long-lived, being stable over a year.

Hydrotropes

Hydrotropes are amphiphilic molecules whose non-polar part is smaller when compared with traditional surfactants (Srinivas et al., *Langmuir* 13 (1997) 3235-3239, which is hereby incorporated by reference in its entirety). In an aqueous environment, hydrotropes do not spontaneously self-assemble to form stable equilibrium structures, unlike surfactants which self-assemble to form stable micelles (Hogdgon et al., *Curr. Opn. Coll. Int. Sci.* 12 (2007) 121-128, which is hereby incorporated by reference in its entirety). However, above a minimum hydrotrope concentration, they show the presence of a loose, dynamic non-covalent clustering or "micelle like" fluctuations (Ooya et al., *Sci. Technol. Adv. Mater.* 6 (2005) 452-456; Cui et al., *J. Pharm. Sci.* 99 (2010) 3048-3060; Hatzopoulos et al., *Langmuir* 27 (2011) 12346-12353; Subramanian et al., *Вестник СПбГу* (Herald of St. Petersburg University) 4 (2013) 140-153, which are hereby incorporated by reference in their entirety). These micelle-like fluctuations are short-ranged, less than 1 nm in size and short-lived with a lifetime of tens of picoseconds (Cui et al., *J. Pharm. Sci.* 99 (2010) 3048-3060; Subramanian et al., *Вестник СПбГу* (Herald of St. Petersburg University) 4 (2013) 140-153; Mijaković et al., *J. Mol. Liq.* 164 (2011) 66-73; Roney et al., *J. Phys. Chem. B* 108 (2004) 7389-7401, which are hereby incorporated by reference in their entirety).

Hydrotropes are classified as ionic and non-ionic hydrotropes, with aromatic ionic hydrotropes, such as sodium benzene sulphonate or sodium benzoate, being traditionally used in the industry (Eastoe et al., *Soft Matt.* 7 (2011) 5917-5925, which is hereby incorporated by reference in its entirety). Although there is a large amount of experimental studies on ionic hydrotropes, the role of the micelle-like fluctuations in aqueous solutions of non-ionic hydrotropes is rarely discussed. Examples of non-ionic hydrotropes include aromatic alcohols such as resorcinol, and amides such as urea (Roy et al., *Curr. Sci.* 85 (2003) 1148-1155; Dempsey et al., *J. Chem. Soc. Faraday Trans.* 88 (1992) 971-977, which are hereby incorporated by reference in their entirety). Non-ionic hydrotropes include short-chain alcohols such as n-propanol, iso-propanol, tertiary butyl alcohol, 2-butoxyethanol, amines such as 3-methylpyridine, and ethers such as tetrahydrofuran.

Although there are certain similarities between hydrotropic solutions and micellar solutions, such as their amphiphilic nature, their ability to "solubilize" hydrophobic compounds, there are also distinct differences (Srinivas et al., *Langmuir* 1998, 14, 6658-6661; Hatzopoulos et al., *Langmuir* 2011, 27, 12346-12353, which are hereby incorporated by reference in their entirety). Micellar solubilization and hydrotropic solubilization are very different with respect to the amount of solubilizer (i.e. hydrotrope) and solubilizate (i.e. hydrophobic compound). Higher amounts of a hydrotrope, compared to surfactants, are needed to solubilize a hydrophobic compound (Kim et al., *J. Pharm. Sci.* 2010, 99, 3953-3965, which is hereby incorporated by reference in its entirety). The solubilization of hydrophobic components in hydrotropic solutions is not a linear function of the hydrotrope concentration, but exhibits a sigmoidal relationship (Balasubramanian et al., *J. Phys. Chem.* 1989, 93, 3865-3870, which is hereby incorporated by reference in its entirety). The change in surface tension of a hydrophobic component in a hydrotropic solution is more gradual than in micellar solutions (Balasubramanian et al., *J. Phys. Chem.* 1989, 93, 3865-3870, which is hereby incorporated by reference in its entirety). Another distinguishing feature of hydrotropes, vis-à-vis traditional surfactants, is that hydrotropes have a much higher hydrophile-lipophile balance (HLB) (Kim et al., *J. Pharm. Sci.* 2010, 99, 3953-3965, which is hereby incorporated by reference in its entirety).

The hydrotropes of the present invention could be non-ionic. For example, the hydrotrope can be methanol, ethanol, isopropanol, tertiary butanol, 2-butoxyethanol, 3-methylpyridine, urea, ethanolamine, trimethylamine, acetone, dioxane, tetrahydrofuran, acetic acid, acetonitrile, ethylene glycol, glycerol, dimethyl sulphoxide, alpha-cyclodextrin, glucose, niacinamide, isobutyric acid.

Hydrophobe-Rich Core

The hydrophobe-rich core as described in the present invention includes at least one hydrophobic organic molecule. Hydrophobic organic molecules of the present invention tend to be non-polar and, thus, prefer non-polar solvents. The hydrophobic interaction is mostly an entropic effect originating from the disruption of highly dynamic hydrogen bonds between molecules of liquid water by the nonpolar solute. By aggregating together, nonpolar molecules reduce the surface area exposed to water and minimize their disruptive effect. Thus, the two immiscible phases (hydrophilic vs. hydrophobic) will change so that their corresponding interfacial area will be minimal. This effect can be visualized in the phenomenon called phase separation.

The hydrophobic organic molecules according to the present invention can be, for example, drugs, active ingredients used in cosmetic formulations, agrochemicals and the like. Many drugs and drug candidates are poorly water-soluble, which limits their clinical applications. A "poorly water-soluble" drug (or simply "poorly soluble" drug) refers to a "practically insoluble" drug in the U.S. Pharmacopeia. It can be defined as a drug having a water solubility of less than 0.1 mg/ml (or 100 μg/ml). Whenever the drug concentration is much less than 0.1 mg/ml, its oral absorption is usually poor or at least inconsistent.

Certain representative drugs which can be used for the purposes of the present invention, i.e., drugs having water-solubility of less than 100 μg/ml at 37° C., are Tolbutamide, Thalidomide, Chloramphenicol, Diclofenac, Digoxin, Hydrocortisone, Phenacetin, Dexamethasone, Quinidine, Griseofulvin, Nifedifine, Phenytoin, Spironolactone, Mebendazole, Chlorpromazine, Nicardipine, Norethindrone, Paclitaxel, Estrone, Reserpine, Progesterone, Terfenadine, Trifluoperazine, Indomethacin, Pimozide, Cinnarizine, Diethylstilbestrol, Flunarizine, Tamoxifen, Itraconazole, Rapamycin. Other poorly soluble drugs include alprostadil, amphotericin B, camptothecin, cosalane, chloramphenicol, cyclosporine, dexamethasone, diazepam, digoxin, epirubicin, glucocorticosteroids, HIV-1 protease inhibitors, palmitoylrhizoxin, p-boronophenylalanine, pregnanolone, and propofol.

Certain embodiments of hydrophobic organic molecules of the present invention include cyclohexane, methyltert-butylether, butylhydroxutoluene. In an embodiment the concentration of the hydrophobic organic molecule in the aqueous solution of the present invention is in the range of $10^{-6}$ mol % to 25 mol %. In one embodiment the hydrophobic molecules of the present invention are not charged.

Hydrogen Bonded Outer Shell

The structure of the colloidal particles of the present invention is such that they contain a hydrophobe-rich core surrounded by a microemulsion-like hydrogen bonded shell of hydrotrope and water molecules. The shell can be regarded as a "protective layer" consisting of hydrotrope and water molecules, which separate the oily core of the hydrophobe-rich molecules from the aqueous-rich bulk phase of the solution.

On the addition of a hydrophobe, the short-lived micelle-like clusters that originally exist in hydrotrope-water binary solutions (such as in TBA-water) are stabilized and rearranged. Over a certain (very small) concentration of hydrophobe, the hydrophobe molecules start to aggregate. Part of the hydrotrope-water clusters surround the hydrophobe aggregates (also called hydrophobe-rich core), protecting them from the water-rich environment. The numbers of clusters, which surround the hydrophobe, depend on the overall amount of the hydrophobe in solution. Thus, the mesoscopic droplets or particles are viewed as having a hydrophobe-rich core, surrounded by a hydrogen-bonded "microemulsion-like" water-hydrotrope shell. The schematic of such a droplet is shown in FIG. 16.

In one embodiment of the present invention, the outer shell has a life time of at least 1 ms. In general, life-time of a structure is determined either from molecular dynamics simulations or experimental techniques such as dynamic light scattering or neutron spin echo. In the present invention MD simulations showed that the structure of the mesoscale droplets formed was stable for as long as the simulations were carried out.

In one embodiment, the mesoscale colloidal particles have a hydrogen bonded outer shell which includes at least one hydrotrope layer that is closest or immediately adjacent to the hydrophobe-rich core. This hydrotrope layer primarily contains hydrotrope molecules. The layer consists of primary and secondary layers surrounding the hydrophobe-rich core. These primary and secondary layers of hydrotrope are further surrounded by a water layer. The water layer primarily consists of water molecules. The layer solvates the primary and the secondary hydrotrope layers. See FIG. 13. Element 1302 forms the primary and the secondary layer of TBA molecules, element 1304 forms the layer of water molecules, and element 1306 forms the tertiary layer of TBA molecules.

In one embodiment, the aqueous solution of the present invention which comprises of mesoscopic colloidal particles is such that the hydrotrope is present at a concentration where the binary solution of water and the hydrotrope shows transient behavior. Transient behavior is a phenomenon where the binary solution including water and a hydrotrope forms micelle like structural entities which have a length scale of less than 1 nm and a life time of 10-100 picoseconds. For example, see FIG. 1.

The hydrotrope could also be present at a concentration range where the binary solution of hydrotrope and water exhibits anomalies in its thermodynamic properties. For example, aqueous TBA solutions, in about 3-8 mol % TBA concentration range and about 0° C.-25° C. temperature range, show the presence of short-ranged (~0.5 nm), short-lived (tens of picoseconds) molecular clusters which result in anomalies of the thermodynamic properties. Anomalies include maximum in solution heat capacity, minimum in isothermal compressibility of solution, minimum in partial molar volume of TBA, minimum in partial molar enthalpy of TBA, minimum in activity coefficient of TBA.

These clusters are transient but do not relax by diffusion, thus are distinctly different from conventional concentration fluctuations. In yet another embodiment, the hydrotrope could be present in a concentration range of 1 mol % to 40 mol %, preferably in the range of 5 mol % to 35 mol %, or in the range of 10 mol % to 30 mol %. More preferably, the range of concentration of the hydrotrope can be 15 mol % to 25 mol % or 20 mol % to 25 mol %.

In one embodiment, the mesoscale colloidal particles and/or the aqueous solutions containing the mesoscale colloidal particles do not include a surfactant, a polymer, a charged molecule such as ionic species, or a liquid crystal. In another embodiment the mesoscale colloidal particles of the present invention have a diameter in the range of 100 nm to 1 μm.

The present invention is also related to a method of making an aqueous solution which includes mesoscale colloidal particles. The method includes adding water, at least one hydrotrope, and a hydrophobic organic molecule to form a mixture and allowing the mixture to form an aqueous solution including at least one mesoscale colloidal particle. Making such solutions does not require addition of surfactants, polymers, charged species such as ions, liquid crystals, or viscosity modifiers such as wax, petrolatum. This offers benefits such as avoiding the need for unnecessary addition of multiple chemicals to a solution and providing an inexpensive method of making solutions by reducing costs associated with addition of multiple chemicals to the solution.

In one embodiment, the method of making the colloidal solution of the present invention involves adding water to at least one hydrotrope to make a first binary solution and then adding at least one hydrophobic organic molecule to the first binary solution of hydrotrope and water in order to make mesoscopic colloidal particles. In another embodiment, the method involves adding at least one hydrophobic organic molecule to at least one hydrotrope to make a second binary solution and then adding water to the second binary solution of hydrophobe and hydrotrope in order to make mesoscopic colloidal particles.

In an embodiment, the methods of the present invention do not include methods such as micronization, milling, bashing, or grinding of the organic hydrophobic molecules or the hydrotropes.

Using the methods of the present invention, the size and the poly dispersity of the colloids can be easily controlled. The colloid described in the present invention can be easily created by cooling the system, without the need for any special process to manufacture the colloids. It has been observed that as the temperature is lowered, the size of the droplets do not change significantly, but their number increases (as observed by an enhancement in the light scattering intensity) (Subramanian et al., *J. Chem. Eng. Data*, 56 (2011) 1238-1248, which is hereby incorporated by reference in its entirety). As the temperature is raised, these droplets disappear, but are observed again when the system is cooled. This phenomenon, manifested by the slow mode in dynamic light scattering, is termed the mesoscale solubilization. Mesoscale solubilization can be defined as the formation of mesoscopic droplets (order of a hundred nm in size) that leads to increased effective solubility of hydrophobic compounds in aqueous solutions of non-ionic hydrotropes.

Colloids could be formed by cooling down the ternary system to 5 or 10° C., from room temperature. The size of the colloidal particles can be controlled from about 100 nm to about a micron, by adjusting the rate of cooling (for example, in the range of 0.1° C./min to 1° C./hr or preferably in the range of 3° C./min to 5° C./hr). Experiments have also shown that this colloidal dispersion is highly stable for many months, making this process promising for various applications. The systems of the present invention can be used for solubilizing hydrophobic organic molecules when polymeric additives cannot be added to the system. Furthermore, the method can be used if one needs to create an inexpensive standard for particles sizing.

EXAMPLES

The following Examples are intended to be illustrative and in no way are intended to limit the scope of the present invention.

Example 1

Materials and Methods for Examples 2-6

TBA with a labeled purity of 0.998+ was purchased from Alfa Aesar. Propylene oxide (PO) with a labeled purity of 0.995+ was purchased from Sigma Aldrich. Isobutyl alcohol (IBA) with a labeled purity of 0.999+ was purchased from J. T. Baker. Cyclohexane (CHX) with a labeled purity of 0.990+ was purchased from Merck. Deionized water was obtained from a Millipore setup.

For light scattering experiments, the binary TBA-water solutions were filtered with 200 nm Nylon filters to remove dust particles. An additional filtration with 20 nm Anopore filters was carried out only if the TBA-water solutions showed mesoscopic droplets due to the presence of hydrophobic impurities in TBA (as shown in Subramanian et al., *J. Phys. Chem. B* 115 (2011) 9179-9183, which is hereby incorporated by reference in its entirety). The third component, PO, IBA or CHX was added to the filtered TBA-water solution. PO was used without filtration because of its high volatility (boiling point 34° C. (Wickert et al., *Chem. Eng. Prog. Sym. Serv. No.* 2. 48 (1958) 92-96, which is hereby incorporated by reference in its entirety)), while IBA and CHX were used after filtering them with 200 nm Nylon filters. Light scattering measurements were performed after equilibrating the samples for about 24 hours.

The refractive index was measured with an Abbe refractometer. The viscosity of the samples was measured with an Ubbelohde viscometer in a temperature controlled (±0.2° C.) water bath.

Example 2

Determination of Phase Diagram

The ternary phase diagram for each of the three systems was determined by the cloud-point method (Othmer et al., *Ind. Eng. Chem.* 33 (1941) 1240-1248, which is hereby incorporated by reference in its entirety). The third component was added to a binary mixture in small steps. At each step, the ternary mixture was manually shaken and let to rest for about 3 to 5 minutes. The sample was then visually observed to determine if phase transition had occurred. If not, more of the third component was added and the above procedure was repeated. The ternary phase diagram of TBA-water-PO system was determined at 25° C., with an accuracy of ±0.1° C. The phase diagrams of TBA-water-IBA and TBA-water-CHX were determined at 21° C., with an accuracy of ±0.5° C. In order to estimate the location of the critical point, light scattering experiments were carried out in the macroscopic one-phase region close to the binodal curve. If the correlation length of critical fluctuations exhibited a maximum, then the point of the binodal curve corresponding to this maximum was interpreted as the critical point.

Example 3

Light Scattering

Static and dynamic light scattering experiments were performed with a PhotoCor Instruments setup, as described in Subramanian et al., *J. Chem. Eng. Data,* 56 (2011) 1238-1248, which is hereby incorporated by reference in its entirety. Temperature was controlled with an accuracy of ±0.1° C. For two exponentially decaying relaxation processes, the intensity auto-correlation function $g_2(t)$ (obtained in the homodyning mode) is given by (Berne et al., Dynamic Light Scattering: With Applications to Chemistry, Biology, and Physics; Wiley N.Y., 1976; Dover Publ., Mineola, N.Y., 2000; Chu, Laser Light Scattering: Basic Principles and Practice; 2nd Edition, Academic Press, Boston 1991, which are hereby incorporated by reference in their entirety)

$$g_2(t) - 1 = \left[A_1 \exp\left(\frac{t}{\tau_1}\right) + A_2 \exp\left(\frac{t}{\tau_2}\right)\right]^2 \quad (1)$$

where $A_1$ and $A_2$ are the amplitudes of the two relaxation processes, t is the "lag" (or "delay") time of the photon correlations and $\tau_1$ and $\tau_2$ are the characteristic relaxation times. For a diffusive relaxation process, the relaxation time is related to the diffusion coefficient, D, as (Berne et al., Dynamic Light Scattering: With Applications to Chemistry, Biology, and Physics; Wiley N.Y., 1976; Dover Publ., Mineola, N.Y., 2000; Chu, Laser Light Scattering: Basic Principles and Practice; 2nd Edition, Academic Press, Boston 1991, which are hereby incorporated by reference in their entirety)

$$\tau = \frac{1}{Dq^2} \quad (2)$$

where q is the difference in the wave number between incident and scattered light, $$q = \left(\frac{4\pi n}{\lambda}\right) \sin\left(\frac{\theta}{2}\right),$$

n is the refractive index of the solvent, λ is the wavelength of the incident light in vacuum (λ=633 nm for the set-up) and θ is the scattering angle. For monodisperse, spherical Brownian particles the hydrodynamic radius R can be calculated with the Stokes-Einstein relation (Berne et al., Dynamic Light Scattering: With Applications to Chemistry, Biology, and Physics; Wiley N.Y., 1976; Dover Publ., Mineola, N.Y., 2000; Chu, Laser Light Scattering: Basic Principles and Practice; 2nd Edition, Academic Press, Boston 1991, which are hereby incorporated by reference in their entirety):

$$R = \frac{k_B T}{6\pi \eta D} \quad (3)$$

where $k_B$ is Boltzmann's constant, T is the temperature and η is the shear viscosity of the medium.

Example 4

Results

Figure 1:
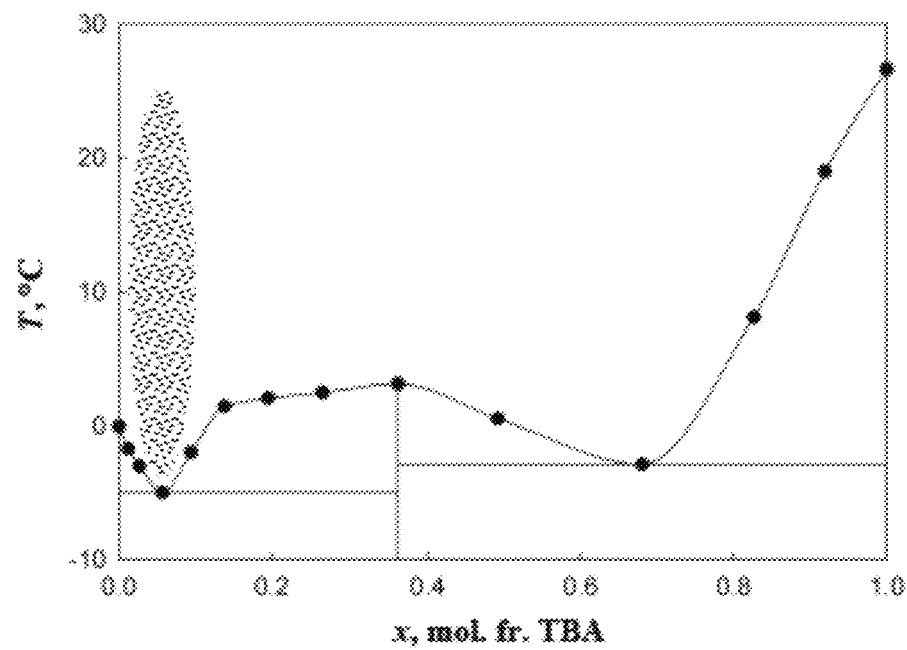
FIG. 1 shows solid-liquid phase diagram of Tertiary Butyl Alcohol (TBA)-water solutions at ambient conditions (based on experimental data from Kasraian et al., *Pharm. Res.* 12 (1995) 484-490, which is hereby incorporated by reference in its entirety). The dotted area schematically shows the region where molecular clustering and thermodynamic anomalies are reported. This area also corresponds to the temperature and concentration region where mesoscale solubilization is observed in TBA-water-hydrophobe solutions.

FIG. 1 shows the liquid-solid phase diagram of TBA-water solutions at ambient pressure, as determined by Kasraian et al. (*Pharm. Res.* 12 (1995) 484-490, which is hereby incorporated by reference in its entirety). TBA and water are completely miscible under ambient conditions. The dotted region of this figure denotes the concentration and temperature range where micelle-like fluctuations (dynamic molecular clustering) and thermodynamic anomalies are reported for TBA-water solutions (Anisimov et al., *J. Struct. Chem.* 19 (1977) 663-670; De Visser et al., *Can. J. Chem.* 55 (1977) 856-862; Koga, *Can. J. Chem.* 1988, 66, 3171-3175; Koga, *Can. J. Chem.* 64 (1986) 206-207; Koga, *Can. J. Chem.* 66 (1988) 1187-1193; Koga et al., *J. Phys. Chem.* 94 (1990) 7700-7706, which are hereby incorporated by reference in their entirety). At this concentration and temperature range, when a small amount of a hydrophobe is added to TBA-water solutions (or a commercial TBA sample is contaminated by hydrophobic impurities) mesoscopic droplets are observed (Subramanian et al., *J. Chem. Eng. Data*, 56 (2011) 1238-1248; Subramanian et al., *J. Phys. Chem. B* 115 (2011) 9179-9183, which are hereby incorporated by reference in their entirety).

Figure 2:
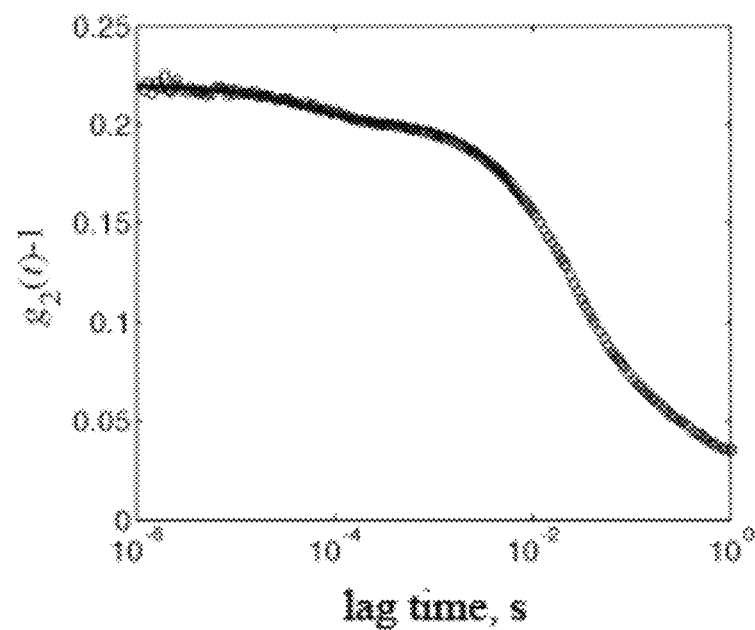
FIG. 2 shows intensity auto-correlation function obtained from dynamic light scattering for a TBA-water-Cyclohexane (CHX) solution at T=25° C. and a scattering angle of θ=45°. Sample concentration is 0.001 mass fraction CHX and 0.26 mass fraction TBA. The black line is a fit to Eq. (1). The correlation function shows the presence of two exponential relaxation processes. A fast process, with a relaxation time of 80 μs and a slow process with a relaxation time of 22 ms.

FIG. 2 shows the intensity auto-correlation function obtained for a TBA-water-CHX solution at T=25° C. and scattering angle θ=45° (q=107 m$^{-1}$). The sample concentration is 0.001 mass fraction CHX and 0.26 mass fraction TBA. FIG. 2 shows the presence of two exponential relaxation processes—a fast process with a relaxation time of 80 μs and a slow process with a relaxation time of 22 ms. In addition, FIG. 2 also shows the presence of a non-exponential tail of long-time relaxations. The fast process corresponds to the molecular diffusion, with a diffusion coefficient of 1.2×10$^{-6}$ cm$^2$/sec, which, in accordance to Eq. (3), corresponds to a hydrodynamic radius (correlation length) of about 0.7 nm. The slower process, with a relaxation time of 22 ms, also exhibits diffusive behavior (as shown for a similar system in previous work (Subramanian et al., *J. Chem. Eng. Data*, 56 (2011) 1238-1248, which is hereby incorporated by reference in its entirety), with an average diffusion coefficient of 4.1×10$^{-9}$ cm$^2$/sec. This relaxation corresponds to the Brownian diffusion of mesoscopic droplets having an average hydrodynamic radius of about 200 nm, but also displaying some polydispersity (D. Subramanian, Ph.D. Dissertation, University of Maryland, College Park, 2012, which is hereby incorporated by reference in its entirety). It has been observed that as the temperature is lowered, the size of the droplets do not change significantly, but their number increases (as observed by an enhancement in the light scattering intensity) (Subramanian et al., *J. Chem. Eng. Data*, 56 (2011) 1238-1248, which is hereby incorporated by reference in its entirety). As the temperature is raised, these droplets disappear, but are observed again when the system is cooled. These droplets are highly long-lived, stable over a year. This phenomenon is called, manifested by the slow mode in dynamic light scattering, the mesoscale solubilization. The longtime tail of the correlation function may be due to the presence of occasionally occurring large aggregates of the order of tens of microns.

In order to understand the mesoscale solubilization further, macroscopic and mesoscopic ternary phase behavior of three different systems, TBA-water-PO, TBA-water-IBA, and TBA-water-CHX, were studied. In each of these three systems, the hydrophobe is completely miscible with TBA, but exhibits partial miscibility with water. PO exhibits the smallest miscibility gap with water (Wickert et al., *Chem. Eng. Prog. Sym. Serv.* No. 2. 48 (1958) 92-96, which is hereby incorporated by reference in its entirety), CHX is almost immiscible with water (C. McAuliffe, *J. Phys. Chem.* 70 (1966) 1267-1275, which is hereby incorporated by reference in its entirety), while the solubility of IBA in water is intermediate (Ott, et al., *J. Chem. Thermodyn.* 11 (1979) 739-746, which is hereby incorporated by reference in its entirety). The ternary phase diagram of TBA-water-PO system is shown in FIG. 3A. The region inside the binodal curve is the two-phase region, while the region outside the binodal curve is the macroscopically homogeneous one-phase region. Various samples within the one-phase region were prepared and analyzed by static and dynamic light scattering. The dotted area of the ternary phase diagram corresponds to a region where the light scattering intensity is at least an order of magnitude higher than the intensity observed for the corresponding binary systems. Additionally, the dynamic auto-correlation functions obtained from this region show the presence of mesoscopic droplets, with a hydrodynamic radius of about 100 nm. This phenomenon is attributed to the mesoscale solubilization.

FIGS. 3B and 3C show the TBA-water-IBA and TBA-water-CHX phase diagrams, respectively. The dotted areas in these figures correspond to mesoscale solubilization, where mesoscopic droplets, with a hydrodynamic radius of about 100 nm are detected by dynamic light scattering.

To further distinguish between mesoscale solubilization and molecular diffusion, intensity auto-correlation functions for three samples from the TBA-water-IBA system at T=10° C. and scattering angle θ=45° (q=1.1×10$^7$ m$^{-1}$) are shown in FIG. 4. The concentrations of the three samples are shown in Table 1 shown below.

TABLE 1

Concentrations of TBA-water-IBA samples studied in this work.
Their correlation functions are shown in FIG. 4

| Sample # | Mass Fr. TBA | Mass Fr. Water | Mass Fr. IBA |
|---|---|---|---|
| A | 0.29 | 0.60 | 0.11 |
| B | 0.26 | 0.65 | 0.09 |
| C | 0.10 | 0.86 | 0.04 |

The correlation functions from samples A and B show the presence of a single exponential relaxation process, corresponding to molecular diffusion. These samples exhibit a diffusion coefficient of 7.0×10$^{-8}$ cm$^2$/sec and 1.6×10$^{-7}$ cm$^2$/sec, corresponding to a hydrodynamic radius of 5 nm and 2 nm, respectively. Sample A is closer to the critical point of the solution and hence exhibits larger concentration fluctuations (manifested by the larger correlation length and slower diffusion). The intensity auto-correlation function from sample C shows the presence of an additional slow relaxation process, associated with the mesoscale solubilization. The mesoscopic droplets have an average hydrodynamic radius of about 130 nm and an average diffusion coefficient of 6.7×10$^{-12}$ cm$^2$/sec.

Example 5

Discussion

The following discussion provides details regarding solubility and differentiates between molecular solubility, mesoscale solubilization, and macrophase separation. Molecular solubility of nonpolar solutes (hydrophobes) in water can be explained by the phenomenon of hydrophobic hydration (Pratt et al., *J. Chem. Phys.* 67 (1977) 3683-3704; Lum et al., *J. Phys. Chem. B* 103 (1999) 4570-4577, which are hereby incorporated by reference in their entirety). Water molecules surrounding a nonpolar solute form a hydrogen-bonded shell around the solute molecule. This shell is similar to a clathrate shell and the water molecules in the shell do not interact strongly with the nonpolar solute in the core (Finney et al., *Biophys. Chem.* 105 (2003) 391-409, which is hereby incorporated by reference in its entirety). However molecular solubility in aqueous solutions of nonionic hydrotropes is quite different, driven by strong interactions between solute and water molecules.

Molecular solubility in aqueous solutions of nonionic hydrotropes can be explained by the concept of clustering. Clustering refers to the formation of transient hydrogen bonds between water molecules and the polar groups of hydrotropes, resulting in micelle-like structural fluctuations. It has been confirmed the formation of such short-ranged (<1 nm), short-lived (tens of picoseconds) clusters in aqueous solutions of TBA (Subramanian et al., *Вестник СПбГу* (Herald of St. Petersburg University) 4 (2013) 140-153, which is hereby incorporated by reference in its entirety). Such clusters are formed due to strong hydrogen bonds between the water molecules and the polar groups of the solute molecules. The hydrogen-bonded network forms a shell structure, which surrounds the nonpolar parts of the solute molecules. Such clusters may have the same length scale as the correlation length obtained from molecular diffusion (when far away from the critical point), but very different dynamics. These clusters do not relax by diffusion, but by the reorientation of hydrogen bonds. They are too fast to be detected by dynamic light scattering (whose time domain is hundreds of nanoseconds and greater), and have too large a wavenumber to be detected by static light scattering.

Molecular diffusion in aqueous hydrotrope solutions has a time scale of about tens of microseconds at q~10$^7$ m$^{-1}$ (far away from the critical point), when probed by dynamic light scattering. Molecular diffusion corresponds to concentration fluctuations (Subramanian et al., *J. Chem. Eng. Data,* 56 (2011) 1238-1248, which is hereby incorporated by reference in its entirety). At a condition far away from the critical point, the length scale of the concentration fluctuations may be of the same order as the length scale of the clusters. However when close to the critical point the correlation length of the concentration fluctuations could reach hundreds of nanometers (the associated relaxation time scale would also increase accordingly). The critical concentration fluctuations can be detected by both static and dynamic light scattering (Berne et al., Dynamic Light Scattering: With Applications to Chemistry, Biology, and Physics; Wiley N.Y., 1976; Dover Publ., Mineola, N.Y., 2000; Anisimov, Critical Phenomena in Liquids and Liquid Crystals; Gordon & Breach Science Publishers, New York, 1991, which are hereby incorporated by reference in their entirety).

Regarding the phenomenon of mesoscale solubilization, the occurrence of mesoscopic droplets (with a length scale of about 100 nm) by mesoscale solubilization of a hydrophobic compound in aqueous hydrotrope solutions occurs at the temperature and concentration range where structural fluctuations are seen in the binary hydrotrope-water solution. The hydrophobic compound stabilizes the structural fluctuations in the hydrotrope-water solution resulting in the formation of mesoscopic droplets. These droplets consist of a hydrophobe-rich core surrounded by a hydrogen bonded water-hydrotrope outer shell. They are highly stable, without any significant change in their size or polydispersity, over long periods of time, from a few months (as in TBA-water-PO system) to over a year (as in TBA-water-CHX system) (Subramanian, Ph.D. Dissertation, University of Maryland, College Park, 2012, which is hereby incorporated by reference in its entirety).

In order to understand the role of the mesoscopic droplets in the thermodynamic stability of the system, various samples were investigated in the two-phase region of the TBA-water-CHX ternary system, when the system has macroscopically phase separated. A ternary sample, whose overall concentration is 0.13 mass fraction TBA and 0.29 mass fraction CHX) was monitored over a period of three months. FIG. 5 shows the auto-correlation functions (obtained from dynamic light scattering) observed in each of the two phases after 3 days of sample preparation. As seen from the figure, the organic layer shows no mesoscopic droplets, while the aqueous layer shows the presence of the mesoscopic droplets of the same size and similar polydispersity as in the macroscopically homogeneous samples (Subramanian, Ph.D. Dissertation, University of Maryland, College Park, 2012, which is hereby incorporated by reference in its entirety). However when monitored over time, it was observed that the light scattering intensity decreased and after three months no mesoscopic droplets were detected in either of the phases. The liquid-liquid interface also did not show any unusual behavior. This indicates that in a two-phase macroscopically separated system, as long as there is an "infinite" reservoir of the hydrophobe-rich phase, the mesoscopic droplets will eventually breakdown, with their constituents joining each of the phases. However, the mesoscopic droplets observed in the macroscopically homogeneous one-phase region are much more stable, remaining unchanged over a period of a year.

Therefore, the observed mesoscale solubilization is a kinetically arrested event rather than a thermodynamically equilibrium phenomenon. The reasons that lead to the apparent stability of the mesoscopic droplets in the macroscopically homogeneous one-phase region may be two-fold. The strong hydrogen bonds between water and hydrotrope molecules shield the hydrophobic core of the droplets thus lowering the effective oil-water surface tension (Israelachvili, Intermolecular and Surface Forces: With Applications to Colloidal and Biological Systems; Academic Press, Orlando, 1985, which is hereby incorporated by reference in its entirety). The shield may also act as a relatively "rigid" membrane, resisting deformation to produce smaller droplets (Safran, Statistical Thermodynamics of Surfaces, Interfaces, and Membranes; Westview Press, Boulder, 2003, which is hereby incorporated by reference in its entirety). Another reason for the high stability of the droplets could be such that in the absence of a large reservoir of the hydrophobe-rich phase, the hydrophobes present in the core of the droplets do not have enough driving force (because of extremely low super saturation) to overcome the hydrogen-bonded shell and form a new phase (Jones, Soft Condensed Matter; Oxford University Press, Oxford, 2002, which is hereby incorporated by reference in its entirety). Hence, under these conditions, the mesoscopic droplets could remain in a kinetically arrested state for very long periods of time, rendering the system practically stable.

However, there is another interesting phenomenon that was observed at the liquid-liquid interface of many hydrotrope-water-hydrophobe systems (Jacob et al., *Phys. Chem. Chem. Phys.* 3 (2001) 829-831, which is hereby incorporated by reference in its entirety). As an example, the interface of one of the TBA-water-CHX samples (whose overall concentrations are 0.16 mass fraction TBA and 0.40 mass fraction CHX) is shown in FIG. 6. This interface seems to harbor a new soap-like "phase." Collecting this "phase" from the macroscopic liquid-liquid interface by a micropipette turned out to be unsuccessful. This novel "phase" may form due to the presence of additional impurities, which attract the mesoscopic droplets towards the interface. In order to verify this hypothesis, a ternary TBA-water-CHX sample was prepared, by using a different source of TBA, one with lower purity (0.997+) than was used for previous sample preparations. When this sample was monitored over a few hours after preparation, the aqueous-rich phase showed the presence of mesoscopic droplets, while the organic-rich phase did not show any droplets. In addition, the interface of this sample showed the presence of the novel "phase".

Example 6

Conclusions

The present invention addresses the ambiguity behind the definition of solubility, differentiates between molecular solubility, mesoscale solubilization, and macrophase separation. Molecular solubility in aqueous solutions of nonionic hydrotropes can be associated with molecular clustering. Clustering exhibits non-diffusive behavior, making and breaking of transient non-covalent bonds between water and hydrotrope molecules. Clustering has a length scale of about a nanometer and a lifetime of about tens of picoseconds. Molecular diffusion is such systems may have a similar length scale (when far away from the critical point), but very different (much slower) dynamics.

In the presence of a hydrophobic compound, structural fluctuations in aqueous solutions of nonionic hydrotropes seem to be stabilized and form mesoscopic droplets. This phenomenon is called mesoscale solubilization. Generally, the mesoscopic droplets are in a kinetically arrested state, remaining stable over a period of a year. Mesoscale solubilization is not unique to the systems studied in this work. Mesoscale solubilization leads to the creation of a novel kind of practically stable colloids, made from small molecules without the addition of surfactants, polymers, emulsifiers, or charged species. Mesoscale solubilization has a variety of applications from encapsulated drug delivery to design and development of various pharmaceutical and cosmetic products.

Unique features in the phenomenon of mesoscale solubilization are the size of the mesoscopic droplets and their stability. The droplets have a characteristic size, of the order of 100 nm. This size does not seem to depend on the type of the hydrophobe or the hydrotrope, nor does it seem to strongly depend on temperature. However, the number of these particles greatly increases as the temperature is lowered.

Example 7

Materials and Methods for Examples 8-16

TBA was procured from two different sources: one source of TBA (with a labeled purity greater than 99.7%) was purchased from Sigma Aldrich, while another source of TBA (with a labeled purity greater than 99.8%) was purchased from Alfa-Aesar. Most of the samples were prepared using the TBA procured from Alfa-aesar, unless otherwise specified. Cyclohexane (CHX), with a labeled purity greater than 99%, was purchased from Merck. Heavy water (used for the SANS experiments), with a labeled purity greater than 99.9 atom %, was purchased from Sigma Aldrich. Deionized water was obtained from a Millipore setup.

For the DLS experiments, the binary solutions of TBA-water were filtered with 200 nm Nylon filters to remove dust particles. In order to eliminate mesoscale inhomogeneities, additional filtrations with 20 nm Anopore filters (at a cold temperature of ~5° C.), were carried out. CHX was used after filtering it through 200 nm Nylon filters. Light-scattering and neutron-scattering measurements were performed after equilibrating the samples for at least 24 hours and further monitoring was conducted for a period of several months or longer.

SANS experiments were performed by using the NG3 SANS instrument at the NIST Center for Neutron Research. The SANS experiments were carried out on TBA-heavy water solutions and on TBA-heavy water-CHX solutions. The concentrations of the samples studied by SANS are presented in Table 3.

TABLE 3

Concentrations of the samples studied by SANS and results from fits to Eq. (7) and (8)

| Sample # | TBA (mol %) | Water (mol %) | CHX (mol %) | Temperature (K) | $\xi_{OZ}$ (nm) | $R_{g\ (fixed)}$ (nm) |
|---|---|---|---|---|---|---|
| Binary | | | | | | |
| SB1 | 3.5 | 96.5 | 0 | 298 | 0.06 | |
| SB2 | 5 | 95 | 0 | 298 | 0.24 | |
| SB3 | 7.4 | 92.6 | 0 | 283 | 0.40 | |
| | | | | 298 | 0.50 | |
| | | | | 313 | 0.63 | |
| Ternary | | | | | | |
| ST1 | 7.40 | 92.57 | 0.03 | 298 | 0.5 | 100 |

The essential measurement length scale in SANS is the wavenumber q. The wavenumber is related to the length scale l, as $l=2\pi/q$, with $$q = \left(\frac{4\pi}{\lambda}\right)\sin\left(\frac{\theta}{2}\right),$$

where $\lambda=6$ Å is the neutron wavelength, and $\theta$ is the scattering angle. In our experiments, q was varied from 0.005 to 0.5 Å$^{-1}$, corresponding to length scales from ~1000 Å to ~10 Å.

Example 8

Molecular Dynamics Simulations

MD simulations on models for pure TBA, on TBA-water mixtures and TBA-water-CHX mixtures were performed. The concentration and number of molecules for each system are presented in Table 2.

TABLE 2

Concentrations of the samples studied by MD simulations

| Sample # | TBA (mol %) | Water (mol %) | CHX (mol %) | Temperature (K) | Number of molecules | Time (ns) |
|---|---|---|---|---|---|---|
| Pure - P1 | 100 | 0 | 0 | 283 | 192 | 10 |
| Binary | | | | | | |
| B1 | 1 | 99 | 0 | 285 | 2125 | 50 |
| B2 | 3.8 | 96.2 | 0 | 285 | 2188 | 1000 |
| B3 | 7 | 93 | 0 | 285 | 2266 | 50 |
| B4 | 18 | 82 | 0 | 285 | 2556 | 50 |
| B5 | 40 | 60 | 0 | 285 | 3503 | 50 |
| Ternary | | | | | | |
| T1 | 11.84 | 85.31 | 2.84 | 298 | 8440 | 50 |
| T2 | 17.70 | 79.65 | 2.65 | 298 | 9040 | 50 |

TABLE 2-continued

Concentrations of the samples studied by MD simulations

| Sample # | TBA (mol %) | Water (mol %) | CHX (mol %) | Temperature (K) | Number of molecules | Time (ns) |
|---|---|---|---|---|---|---|
| T3 | 27.78 | 69.44 | 2.78 | 298 | 8640 | 50 |
| T4 | 40.05 | 57.21 | 2.74 | 298 | 8740 | 50 |

The TIP4P-Ew water model (Martínez et al., *J. Comput. Chem.*, 2009, 30, 2157-2164, which is hereby incorporated by reference in its entirety) was used and parameters for TBA and CHX were taken from the CHARMM General Force Field (Vanommeslaeghe et al., *J. Comput. Chem.*, 2010, 31, 671-690, which is hereby incorporated by reference in its entirety). The systems were built by using the Packmol package (Martínez et al., *J. Comput. Chem.*, 2009, 30, 2157-2164, which is hereby incorporated by reference in its entirety), which randomly packs all molecules in a simulation box.

The NAMD simulation program (Phillips et al., *J. Comput. Chem.*, 2005, 26, 1781-1802, which is hereby incorporated by reference in its entirety) was used to perform all MD simulations with 2 fs time steps for a total of 10 to 1000 ns (see Table 2). Most simulations were run for 50 ns, while one binary TBA-water simulations was run longer to determine if any clathrate-like structures would form. The van der Waals interactions were smoothly switched off between 8 and 10 Å by a potential-based switching function. Long-range electrostatic interactions were calculated by using the particle-mesh Ewald (PME) method (Darden, *J. Chem. Phys.*, 1993, 98, 10089-10092, which is hereby incorporated by reference in its entirety). An interpolation order of 4 and a direct space tolerance of 10-6 were used for the PME method. Langevin dynamics was used to maintain constant temperatures for each system, while the Nosé-Hoover Langevin-piston algorithm (Feller et al., *J. Chem. Phys.*, 1995, 103, 4613-4621; Martyna et al., *J. Chem. Phys.*, 1994, 101, 4177-4189, which are hereby incorporated by reference in their entirety) was used to maintain constant pressure at 1 bar. The Visual Molecular Dynamics (VMD) program (Humphrey et al., *J. Mol. Graphics*, 1996, 14, 33-38, which is hereby incorporated by reference in its entirety) was used to create snapshots and to calculate the radial distribution functions (RDF).

Example 9

Dynamic Light Scattering

DLS experiments were performed with a PhotoCor Instruments setup, as described in ref. (Subramanian et al., *J. Chem. Eng. Data*, 2011, 56, 1238-1248, which is hereby incorporated by reference in its entirety) Temperature was controlled with an accuracy of ±0.1° C. For two exponentially decaying relaxation processes, the intensity auto-correlation function $g_2(t)$ (obtained in the homodyning mode) is given by (Berne and Pecora, Dynamic Light Scattering: With Applications to Chemistry, Biology, and Physics, Wiley, New York, 1976; Dover Publications, Mineola, N.Y., 2000; Chu, Laser Light Scattering: Basic Principles and Practice, Academic Press, Boston 1991 which are hereby incorporated by reference in their entirety)

$$g_2(t) - 1 = \left[A_1\exp\left(\frac{t}{\tau_1}\right) + A_2\exp\left(\frac{t}{\tau_2}\right)\right]^2 \quad (4)$$

where $A_1$ and $A_2$ are the amplitudes of the two relaxation processes, t is the "lag" (or "delay") time of the photon correlations and $\tau_1$ and $\tau_2$ are the characteristic relaxation times. For a diffusive relaxation process, the decay rate ($\Gamma$) is related to the diffusion coefficient D, as:

$$\Gamma = \frac{1}{\tau} = Dq^2 \quad (5)$$

where q is the difference in the wavenumber between incident and scattered light, $$\left(\frac{4\pi n}{\lambda}\right)\sin\left(\frac{\theta}{2}\right),$$

n is the refractive index of the solvent, $\lambda$ is the wavelength of the incident light in vacuum ($\lambda$=633 nm for our set-up), and $\theta$ is the scattering angle. For monodisperse, spherical, Brownian droplets the hydrodynamic radius R can be calculated by using the Stokes-Einstein relation:

$$R = \frac{k_B T}{6\pi \eta D} \quad (6)$$

where $k_B$ is Boltzmann's constant, T is the temperature, and $\eta$ is the shear viscosity of the medium.

Example 10

Phase Behavior and Thermodynamics Anomalies of Aqueous Solutions of TBA

FIG. 1 shows the solid-liquid phase diagram of TBA-water solutions at ambient pressure (Kasraian et al., *Pharm. Res.*, 1995, 12, 484-490, which is hereby incorporated by reference in its entirety). While there exist different solid phases, the liquid phase is homogeneous on the macroscopic scale, with TBA and water completely miscible with each other. FIG. 1 also shows the temperature and concentration domain (shaded in grey) where aqueous TBA solutions exhibit micelle-like structural fluctuations and thermodynamic anomalies. Excess and partial molar properties, heat capacity, and isothermal compressibility all exhibit extrema in the solute-rich region of TBA-water solutions. These anomalies occur in the concentration range of 3 to 8 mol % (11 to 26 mass %) TBA and become enhanced below room temperature.

The thermodynamic anomalies provide insight into solute-solvent interactions and on the structural changes that occur at the molecular scale. For example, as shown in FIG. 7, the enthalpy of mixing is negative in the solute-rich region with a minimum at ~6 mol % (21 mass %) TBA, and becomes positive as the TBA concentration is increased (Koga, *Can. J. Chem.*, 1988, 66, 3171-3175; Koga, *Can. J. Chem.*, 1986, 64, 206-207; Koga, *Can. J. Chem.*, 1988, 66, 1187-1193 which are hereby incorporated by reference in their entirety). The excess chemical potential of water shows a similar trend (Koga et al., *J. Phys. Chem.*, 1990, 94, 7700-7706; W. S. Knight, Ph. D. Dissertation, Princeton University 1962, which are hereby incorporated by reference in their entirety). These anomalies indicate that at low TBA concentrations, solute-solvent interactions are favorable, with water and TBA molecules preferring to couple with each other. As the TBA concentration is increased, solute-solute and solvent-solvent interactions are favored over solute-solvent interactions, indicating that TBA and water molecules prefer to demix.

The heat capacity of aqueous TBA solutions also exhibits anomalies, with maxima observed in the solute-rich region (Anisimov et al., *J. Struct. Chem.*, 1977, 18, 663-670; De Visser et al., *Can. J. Chem.*, 1977, 55, 856-862, which are hereby incorporated by reference in their entirety). The maxima become sharper as the temperature is lowered (Tamura et al., *Phys. Chem. Chem. Phys.*, 1999, 1, 121-126, which is hereby incorporated by reference in its entirety). This could be an indication of a structural change in this region. Remarkably, as most recent experiments have demonstrated, this heat capacity anomaly is rather insensitive to the presence or absence of mesoscale inhomogeneities (the anomaly persists even after the mesoscale inhomogeneities have been eliminated by filtration). This indicates that the heat capacity anomaly is inherent to the molecular structure of binary TBA-water solutions, and is not significantly affected by the presence (or absence) of mesoscale inhomogeneities.

Thermodynamic anomalies have also been observed in aqueous solutions of many other hydrotropes. Aqueous solutions of other alcohols such as methanol, ethanol, n-propanol, isopropanol, and 2-butoxyethanol all show similar anomalies in their thermodynamic properties within the water-rich region. In TBA-water solutions, these anomalies are most pronounced (Franks et al., *Q. Rev. Chem. Soc.*, 1966, 20, 1-44, which is hereby incorporated by reference in its entirety). These thermodynamic anomalies can be attributed to structural fluctuations (clustering) occurring on the molecular scale (Subramanian et al., *Вестник СПбГу* (Herald of St. Petersburg University), 2013, 4, 140-153, which is hereby incorporated by reference in its entirety). MD simulations of TBA-water solutions, presented in the following section, support this view.

Example 11

Molecular-Scale Clustering in Aqueous Solutions of TBA

MD simulations were performed on models of pure TBA and aqueous solutions of TBA. In the aqueous solutions, the concentration of TBA was varied from 1 to 40 mol % (4 to 73 mass %). FIG. 8A shows the radial distribution functions (RDFs) between the central carbons of TBA in pure TBA and in aqueous solutions of TBA. In pure TBA, there exists a peak at a distance of 4.7 Å and a second peak at a distance of 6 Å. The first peak in the RDF corresponds to strong van der Waals interactions, while the second peak corresponds to weaker van der Waals interactions between the methyl groups of TBA.

In the aqueous solutions, the first peak (at 4.7 Å) between central C atoms of TBA disappears, but the peak at 6 Å becomes enhanced. This indicates, in agreement with thermodynamic anomalies, that in aqueous solutions, TBA molecules prefer to interact with water rather than with other TBA molecules. It is also observed that the magnitude of this peak increases as the TBA concentration is increased. This is an indication that at higher TBA concentrations more number of TBA molecules "cluster" together at this distance. Secondary and tertiary peaks are also seen in aqueous TBA solutions, which differ from simulations of pure TBA. As the concentration of TBA increases, the secondary peak occurring at 8 Å tends to disappear. This could be an indication that at higher concentrations aqueous TBA solutions do not form "isolated clusters" with water or that the clustering with water has changed in a TBA-rich solution.

FIG. 8B shows the RDFs between the oxygen atom of TBA and the oxygen atom of water in aqueous solutions of TBA and between oxygen atoms of TBA in the pure TBA system. This figure shows a large initial peak at 3 Å in pure TBA, which disappears in aqueous solutions. An initial peak between water and TBA is seen in aqueous solutions at 2.6 Å. This again indicates that in aqueous solutions, TBA tends to form hydrogen bonds with water rather than with itself. Moreover, the distance is shorter indicating stronger hydrogen bond with water than between TBA-TBA. As the concentration of TBA increases, the magnitude of the first peak increases. This indicates that there is a stronger preference for water to form hydrogen bonds with the hydroxyl of TBA at these higher concentrations. As the TBA concentration is raised, the secondary peak, which occurs at 4.4 Å, increases while the tertiary and higher peaks almost disappear. This indicates that at higher TBA concentrations the water molecules surrounding the TBA molecules in tertiary shells and beyond are not very well defined and the resultant "cluster" loses its structural integrity.

Snapshots from MD simulations can help in interpreting the RDFs as shown in FIG. 9. At the lower concentrations, TBA forms clusters due to van der Waals interactions between its methyl groups. These TBA clusters are surrounded by a hydrogen-bonded polygonal (either pentagonal (FIGS. 9B, 9C) or hexagonal (not shown)) network formed between TBA-water and water-water molecules. The main RDF peak at 6 Å, as seen in FIG. 8A, corresponds to the distance between central carbon atoms of TBA, which may be dimers, trimers or tetramers of TBA. The secondary peak at 8 Å, as seen in FIG. 8A, corresponds to a distance between the central carbon atoms in oligomerized TBA with its nearest neighbor of unstructured TBA. The water molecules are organized in a specific hydrogen-bonded structure around TBA molecules, with the hydroxyl group of the TBA molecules forming one of the vertices of a hydrogen-bonded polygon.

The structural significance of the peaks calculated in the O(TBA)-O(Water) RDFs of FIG. 8B can be visualized from the snapshots in FIG. 9. The primary peak in FIG. 8B is from 3 waters coordinating the hydroxyl group of TBA. The secondary RDF peak at 4.4 Å and the tertiary peak at 5.6 Å in FIG. 8B correspond to larger distances between the vertices in the pentagon and/or hexagon ring of water. The secondary and tertiary peaks correspond to an additional 17-21 surrounding water molecules. This leads to an effective structure, which is called as a "micelle-like cluster." The cluster has an inner radius of ~4 Å that constitutes 4 to 5 TBAs and an additional distance including water shells of ~6.5 Å. Thus, this "micelle-like cluster" constituting TBA and water molecules is ~10.5 Å in radius. Although the water structures surrounding TBA form polygons commonly found in hydrates (Sloan and Koh, Clathrate Hydrates of Natural Gases, Taylor and Francis, Boca Raton, Fla., 2008, which is hereby incorporated by reference in its entirety), the micelle-like clusters are short-lived and appear to be transient, with an estimated lifetime of the order of 10-50 ps.

The effect of TBA concentration seen from the RDF's of aqueous TBA solutions can also be explained from the snapshots in FIG. 9. At low concentrations, 1 to 2 mol % (4 to 8 mass %) TBA, the average cluster sizes of TBA molecules range from 1 to 4 and the number of clusters tends to be small. TBA forms a micelle-like cluster with water. At higher TBA concentrations, 3 to 7 mol % (11 to 24 mass % TBA), the clusters tend to be larger with 4 to 8 TBA molecules. Bipyramidal structures of TBA clusters (FIG. 9B) transiently exist (20 to 50 ps) at the 3 to 7 mol % concentration range. As the TBA concentration is further raised, the clusters of TBA-water do not behave as a micelle, but rather TBA becomes dominant in terms of volume component in the solution (FIGS. 9D, 9E), reflecting a growing tendency to be apart from water molecules. These solutions no longer have the short-lived TBA-water clusters and instead look more like a randomly mixed solution of TBA and water (usual non-ideal solution). At 40 mol % (73 mass %) TBA, the water concentration is too low to form any significant water polygon structure indicative of the reduction and loss of secondary and higher order peaks in the RDFs (FIG. 8).

Example 12

SANS in Aqueous Solutions of TBA

In order to characterize the molecular-scale inhomogeneities in aqueous solutions of TBA, SANS experiments were carried out on TBA-heavy water solutions. The following equation best fits the SANS intensity data (M. A. Anisimov, Critical Phenomena in Liquids and Liquid Crystals, Gordon & Breach Science Publishers, New York, 1991, which is hereby incorporated by reference in its entirety):

$$I(q) = \frac{A_3}{1 + (\xi_{OZ}q)^2} + B \tag{7}$$

where $A_3$ is the amplitude, B is a background parameter, and $\xi_{OZ}$ is the Ornstein-Zernike correlation length, which characterizes the length scale of concentration fluctuations; it increases as the temperature is raised and as the TBA concentration is increased. This behavior of the correlation length is expected as the system approaches a "virtual" critical point (hidden here by the vapor-liquid transition, but may become real on the addition of a salt, such as KCl) located at an inaccessible higher temperature and higher TBA concentration. FIG. 10A shows the SANS data for various concentrations of TBA at 25° C., while FIG. 10B shows the SANS data for 7.4 mol % (23 mass %) TBA solution at different temperatures. The results from the SANS fits are presented in Table 3. The results obtained for the correlation length are consistent with what has been observed in the literature (Euliss et al., J. Chem. Phys., 1984, 80, 4767-4773, which is hereby incorporated by reference in its entirety).

The micelle-like clusters (structural fluctuations) observed from MD simulations could not be seen from SANS data. Although some spectra at low temperatures suggest the existence of a marginally detectable peak in the structure factor at q~0.1 Å. The reasons for this could be two-fold: poor SANS contrast between these clusters and the bulk solution or small contribution of these clusters into the intensity as compared to the contribution from the concentration fluctuations.

Example 13

DLS and SANS in Aqueous Solutions of TBA Upon the Addition of a Hydrophobe

FIG. 11 shows the intensity auto-correlation function observed from an aqueous solution of TBA (purchased from Sigma Aldrich). The correlation function shows the presence of two relaxation processes—a fast process with a relaxation time of 65 μs and a slow process with a relaxation time of 22 ms. The fast process corresponds to molecular diffusion, with a diffusion coefficient of $1.5 \times 10^{-6}$ cm$^2$/sec. In accordance with Eq. (6), this corresponds to a hydrodynamic radius of about 0.6 nm. This is consistent with the correlation length ($\xi_{OZ}$) of the concentration fluctuations obtained from SANS data as discussed in the previous section.

The slower process, with a relaxation time of 22 ms, corresponds to meso scale inhomogeneities (Subramanian et al., *J. Chem. Eng. Data*, 2011, 56, 1238-1248, which is hereby incorporated by reference in its entirety). As the temperature is increased, this slow mode disappears and reappears as the temperature is lowered. In fact, at low temperatures the contribution from the slow mode is enhanced so significantly, that it becomes quite difficult to detect molecular diffusion. The mesoscale inhomogeneities were only observed between the concentrations 3 to 8 mol % (11 to 26 mass %) TBA. Above this concentration range, the mesoscale inhomogeneities disappeared.

In order to understand the origin of the slow mode, this aqueous TBA solution was filtered multiple times by using a 20 nm Anopore filter, at a low temperature (~5° C.), to eliminate the slow mode. The intensity auto-correlation function obtained after filtering the aqueous TBA solutions at cold conditions is also shown in FIG. 11. The resultant correlation function shows no mesoscale inhomogeneities, but only the contribution from molecular diffusion. A controlled "impurity", namely a trace amount (0.03 mol %) of a third, more hydrophobic, component (cyclohexane) was added to an aqueous TBA solution that initially did not show any mesoscale inhomogeneities. Upon the addition of cyclohexane, mesoscale inhomogeneities emerged, and the slow mode was observed. Various hydrophobic additives such as propylene oxide, isobutyl alcohol, and methyl tert-butyl ether were also studied. All these experiments showed that the slow mode appears only when the aqueous TBA solution contains a more hydrophobic component (Subramanian et al., *J. Phys. Chem. B*, 2011, 115, 9179-9183, which is here by incorporated by reference in its entirety). The wavenumber dependence of the relaxation rate of these inhomogeneities (in accordance with Eq. 5) revealed that they are diffusive Brownian droplets (Subramanian et al., *J. Phys. Chem. B*, 2011, 115, 9179-9183, which is here by incorporated by reference in its entirety). Confocal microscopy images are also consistent with what is observed from dynamic light scattering (Subramanian et al., *J. Chem. Eng. Data*, 2011, 56, 1238-1248, which is hereby incorporated by reference in its entirety).

The presence of mesoscopic droplets can also be verified from SANS experiments. FIG. 12 shows the SANS intensity I(q) from a TBA-heavy water solution containing trace amounts of cyclohexane (CHX) as the hydrophobe. The SANS data in this TBA-heavy water-CHX system were best fit to an equation of the following form (Gompper and Schick, Self-Assembling Amphiphilic Systems, Phase Transitions and Critical Phenomena, Volume 16, Academic Press, London, 1994, which is hereby incorporated by reference in its entirety):

$$I(q) = \frac{A_4}{(R_g q)^4} + \frac{A_5}{1 + (\xi_{OZ} q)^2} + B_1 \qquad (8)$$

where $A_4$ and $A_5$ are the amplitudes, $R_g$ is the radius of gyration of the mesoscopic droplets, $\xi_{OZ}$ is the correlation length of the concentration fluctuations, and $B_1$ is a background parameter. The above equation includes contributions from the Ornstein-Zernike form of concentration fluctuations and contributions from the much larger, mesoscopic droplets. Since the SANS data do not reach a Guinier region (plateau at low q), the $R_g$ corresponding to mesoscopic droplets was fixed at 100 nm (as was observed from DLS).

Example 14

Investigating the Structure of Mesoscopic Droplets by MD Simulations

In order to further investigate the nature of these mesoscopic droplets, MD simulations of TBA-water-CHX solutions were carried out. FIG. 13 shows a snapshot from MD simulations where aggregated CHX molecules are surrounded by TBA molecules. The concentration of TBA in the layer surrounding the CHX aggregate is higher than in the bulk solution. The structure of this layer is similar to a "microemulsion" structure, which seems to occur at higher concentrations of TBA, as seen from simulations (Kežić and Perera, *J. Chem. Phys.*, 2012, 137, 014501-1-11, which is hereby incorporated by reference in its entirety). Water molecules form hydrogen bonds with the hydroxyl groups of the TBA molecules. There may be secondary or higher order layers of TBA and water molecules that surround the CHX aggregate (FIG. 13), leading to the formation of a "droplet". The observed droplets remained stable for the length of the simulation.

Simulations of TBA-water-CHX solutions with different concentrations of TBA, but almost the same concentration of CHX, were also carried out. FIG. 14A shows the RDFs between central carbon atoms of TBA molecules, while FIG. 14B shows the RDFs between central C of TBA molecule and a carbon on the CHX (C1) molecule. FIGS. 15A to 15D show snapshots from MD simulations. The RDFs and the snapshots indicate that as the TBA concentration increases, the tendency to form "droplets" (as described above) disappears. FIGS. 15C and 15D show that at high TBA concentrations, TBA and CHX prefer to remain mixed with each other rather than form droplets.

Example 15

Mesoscale Solubilization—A State Between Molecular Solubility and Macrophase Separation The phenomenon of formation of mesoscopic droplets in aqueous solutions of hydrotropes containing hydrophobes is termed as mesoscale solubilization. Mesoscale solubilization is a distinct intermediate state between molecular solubility and macrophase separation. Molecular solubility of nonpolar solutes (hydrophobes) in water can be explained by the phenomenon of hydrophobic hydration (Stillinger, *J. Solution Chem.*, 1973, 2, 141-158; Pratt et al., *J. Chem. Phys.*, 1977, 67, 3683-3704; Lum et al., *J. Phys. Chem. B*, 1999, 103, 4570-4577, which are hereby incorporated by reference in their entirety), where water molecules form a hydrogen-bonded shell around the solute molecule. This shell is similar to a clathrate shell and the water molecules in the shell do not interact strongly with the nonpolar solute in the core (Lum et al., *J. Phys. Chem. B*, 1999, 103, 4570-4577, which is hereby incorporated by reference in its entirety). However, molecular solubility in aqueous solutions of nonionic hydrotropes is quite different, where the water molecules strongly interact with the solute molecules through strong hydrogen bonds. This interaction leads to the formation of loose micelle-like clusters in water-hydrotrope solutions. Such clusters may have the same length scale as the correlation length of the concentration fluctuations (when far away from the critical point), but very different dynamics. Clusters, which have a life-time of tens of picoseconds, relax by the reorientation of hydrogen bonds, while concentration fluctuations have a time-scale of about tens of microseconds at $q\sim10^7$ m$^{-1}$ (when far away from the critical point) and relax by diffusion. The cluster dynamics can be experimentally detected by neutron spin echo techniques, whereas concentration fluctuations can be detected by SANS (the correlation length) and DLS (the diffusion coefficient).

On the addition of a hydrophobe (such as cyclohexane), the short-lived micelle-like clusters that originally exist in hydrotrope-water binary solutions (such as in TBA-water) seem to be stabilized and rearranged. Over a certain (very small) concentration of hydrophobe, the hydrophobe molecules start to aggregate. Part of the hydrotrope-water clusters surround the hydrophobe aggregates, protecting them from the water-rich environment. The numbers of clusters, which surround the hydrophobe, depend on the overall amount of the hydrophobe in solution. Thus, the mesoscopic droplets are viewed as having a hydrophobe-rich core, surrounded by a hydrogen-bonded "microemulsion-like" water-hydrotrope shell. The schematic of such a droplet is shown in FIG. 16.

In order to understand the thermodynamic stability of the mesoscopic droplets, the macroscopic behavior of the ternary system TBA-water-CHX was studied. The ternary phase diagram at ambient conditions is shown in FIG. 3C. This figure shows that TBA is completely miscible with water and CHX, while water and CHX are almost completely immiscible with each other. The region where mesoscopic droplets are observed is shown in the inset of FIG. 3C. Remarkably, this region corresponds to the concentration range where structural fluctuations and thermodynamic anomalies are observed in binary TBA-water solutions. Mesoscopic droplets are not observed on addition of CHX to pure water or to TBA-water solutions where the TBA concentration is greater than 10 mol %. In the region around 7 mol % TBA the mesoscale droplets are extremely long-lived, being stable for over a year. Only in the presence of a macroscopic hydrophobe-rich phase (samples studied in the two-phase region of the ternary system), these droplets tend to slowly (over a period of months) condense on the water/CHX interface. The instability of the mesoscopic droplets in the presence of the macroscopic water/CHX interface may be due to the destruction of the TBA-water protective shell, which surrounds the hydrophobic CHX core.

Mesoscale solubilization, being intermediate between molecular solubility and macroscopic phase separation, makes the traditional definition of solubility ambiguous. Thus, popular experimental techniques, such as chromatography methods, used for measuring solubility of hydrophobic species in water may be misinterpreted. Moreover, the bulk equilibration may require an unrealistically long time, making the definition of thermodynamic equilibrium also ambiguous.

Example 16

Summary and Conclusions

MD simulations in TBA-water solutions show the presence of short-ranged (~1 nm), short-lived (10 to 50 ps) clusters, interpreted as micelle-like structural fluctuations. These clusters may have a length-scale similar to the concentration fluctuations, but have very different (much faster) dynamics. Concentration fluctuations relax by diffusion, while clusters relax by the reorientation of hydrogen bonds. Clustering is observed in the low concentration region of TBA (1 to 8 mol % or 4 to 26 mass %) and tends to disappear at higher TBA concentrations. These clusters are likely responsible for the thermodynamic anomalies observed in aqueous TBA solutions. The presence of concentration fluctuations was clearly detected by SANS and by DLS techniques.

Mesoscale inhomogeneities, which are Brownian diffusive droplets, order of 100 nm in size, are observed in aqueous solutions of TBA containing a hydrophobic component. The hydrophobe tends to stabilize and rearrange the short-ranged, short-lived structural fluctuations initially present in aqueous TBA solutions and leads to the formation of larger (mesoscopic) droplets. The structure of these droplets is such that they contain a hydrophobe-rich core surrounded by a microemulsion-like hydrogen-bonded shell of TBA and water molecules. The shell can be regarded as a "protective layer" consisting of TBA and water molecules, which separate the oily core of the aggregates from the aqueous-rich bulk phase of the solution. The formation of mesoscopic droplets in aqueous solutions of hydrotropes, containing hydrophobe, is termed as mesoscale solubilization.

Two peculiar features characterize mesoscale solubilization. The mesoscopic droplets are order of 100 nm in size. This size does not seem to significantly depend on the type of the hydrotrope or the hydrophobe. Lowering the temperature enhances the number of these droplets, but their size remains almost unchanged. Moreover, these droplets are extremely long-lived, being stable for over a year. Only in the presence of a macroscopic hydrophobe-rich phase do these droplets tend to slowly (over a period of months) condense on the water/oil interface. The phenomenon observed in aqueous solutions of TBA may represent a ubiquitous feature of aqueous solutions of nonionic hydrotropes, and may have important practical implications in areas such as drug delivery, where traditional surfactants may need to be replaced by hydrotropes.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:
1. A method for making a highly stable colloidal solution comprising:
    mixing water, at least one non-ionic hydrotrope, and at least one hydrophobic organic molecule to form a mixture; and wherein the solution does not include a surfactant, a polymer, or a charged species,
    wherein, the at least one non-ionic hydrotrope is tertiary-butanol, 2-butoxyethanol, or 3-methylpyridine and has a concentration range of 1 mol % to 40 mol %, based on the solution as a whole,
    wherein the at least one hydrophobic organic molecule is cyclohexane, propylene oxide, isobutyl alcohol, methyltertbutylether, or butylhydroxytoluene,
    wherein the at least one hydrophobic organic molecule disrupts highly dynamic hydrogen bonds between mol- ecules of liquid water and has a concentration range of $10^{-6}$ mol % to 25 mol %, based on the solution as a whole, and allowing the mixture to form a highly stable colloid, wherein said highly stable colloid has a particle size of order of 100 nm for at least one year.

2. The method according to claim 1, further comprising a step of cooling the highly stable colloid.

3. The method according to claim 2, wherein cooling is done at a rate of 3° C./min to 5° C./hr.

4. The method according to claim 2, wherein the highly stable colloid is cooled from room temperature to 5° C.

5. The method according to claim 1, wherein the at least one hydrophobic organic molecule and exhibits a water solubility of less than 0.1 mg/ml.

6. The method according to claim 1, wherein the highly stable colloid comprises a plurality of mesoscale particles with a hydrophobe-rich core surrounded by a hydrogen-bonded water-hydrotrope shell.

7. The method of claim 1, wherein the at least one hydrophobic organic molecule is cyclohexane, propylene oxide, or isobutyl alcohol.

8. A method for making a highly stable colloidal solution comprising:

mixing water, at least one non-ionic hydrotrope, and at least one hydrophobic organic molecule to form a mixture; and wherein the solution does not include a surfactant, a polymer, or a charged species, wherein, the at least one non-ionic hydrotrope is tertiary-butanol, 2-butoxyethanol, or 3-methylpyridine and has a concentration range of 1 mol % to 40 mol %, based on the solution as a whole, wherein the at least one hydrophobic organic molecule is cyclohexane, propylene oxide, isobutyl alcohol, methyltertbutylether, or butylhydroxytoluene, wherein the at least one hydrophobic organic molecule disrupts highly dynamic hydrogen bonds between molecules of liquid water and has a concentration range of $10^{-6}$ mol % to 25 mol %, based on the solution as a whole, and allowing the mixture to form a highly stable colloid, wherein said highly stable colloid has a particle size of order of 100 nm for at least one year and the highly stable colloid comprises a plurality of mesoscale particles with a hydrophobe-rich core surrounded by a hydrogen-bonded water-hydrotrope shell.

* * * * *